US010402872B1

(12) United States Patent
Zielske et al.

(10) Patent No.: US 10,402,872 B1
(45) Date of Patent: Sep. 3, 2019

(54) AUTOMATED MEDICAL PROCEDURE CODING AND DOCUMENTATION SYSTEM

(71) Applicant: ZHEALTH DOCUMENTATION 2, LLC, Nashville, TN (US)

(72) Inventors: David R. Zielske, Nashville, TN (US); Ryan Kenton Palmer, Tigard, OR (US)

(*) Notice: Subject to any disclaimer, the term of this patent is extended or adjusted under 35 U.S.C. 154(b) by 529 days.

(21) Appl. No.: 14/510,087

(22) Filed: Oct. 8, 2014

Related U.S. Application Data

(60) Provisional application No. 61/888,147, filed on Oct. 8, 2013.

(51) Int. Cl.
*G16H 10/60* (2018.01)
*G06Q 30/04* (2012.01)
*G06Q 50/22* (2018.01)

(52) U.S. Cl.
CPC ............ *G06Q 30/04* (2013.01); *G06Q 50/22* (2013.01)

(58) Field of Classification Search
CPC .... G06F 19/322–327; G06Q 50/22–24; G06Q 40/00; G06Q 30/04; G16H 10/60
See application file for complete search history.

(56) References Cited

U.S. PATENT DOCUMENTS

| | | | | |
|---|---|---|---|---|
| 6,208,973 | B1* | 3/2001 | Boyer | G06Q 20/02 705/2 |
| 2009/0070140 | A1* | 3/2009 | Morsch | G06F 19/3487 705/2 |
| 2014/0081652 | A1* | 3/2014 | Klindworth | G06Q 10/10 705/2 |

* cited by examiner

*Primary Examiner* — Sheetal R Paulson
(74) *Attorney, Agent, or Firm* — Wayne Edward Ramage; Baker Donelson

(57) ABSTRACT

A system for documenting and coding diagnostic and interventional procedures for hospital and physician reimbursement, and automating the process of documenting and coding so that the two steps are unified into a singular activity. The computer-based system provides a graphical user interface allowing the physician to input details pertinent to the diagnostic and interventional procedures in an interactive manner. The computer program provides active guidance that enforces specification of details required to justify medical necessity of each performed procedure. Based on the physician's procedure entry, the program generates the resulting CPT (Current Procedural Terminology) codes and their accompanying documentation, thereby eliminating the opportunity for error. The program produces reports ready for submission for reimbursement.

8 Claims, 29 Drawing Sheets

AUTOMATED MEDICAL PROCEDURE CODING AND DOCUMENTATION SYSTEM

This application claims benefit of and priority to U.S. Provisional Application No. 61/888,147, filed Oct. 8, 2013, entitled "Automated Medical Procedure Coding and Documentation System," by David Zielske, and is entitled to that filing date for priority in whole or in part. The specification, figures and complete disclosure of U.S. Provisional Application No. 61/888,147 are incorporated herein by specific reference for all purposes.

FIELD OF INVENTION

This invention relates to an automated system and method of documenting and coding diagnostic and interventional procedures for hospital and physician reimbursement.

BACKGROUND OF THE INVENTION

As healthcare costs continue to escalate, issues concerning the efficient and correct coding and documentation of procedures for hospital and physician reimbursement are becoming increasingly important. Coding and documentation of procedures, such as endovascular procedures, today involves several steps, including physicians documenting their procedures using dictation, and medical coders specifying codes for reimbursement based on that dictation. This process is error-prone, as it involves several opportunities for mis-interpretation. For example, the physician may use terms and expressions that can be interpreted differently in their dictation, and physician may omit critical circumstantial information required to justify the medical necessity of performed procedures. This process often results in erroneous claims being submitted by the hospitals and physicians.

SUMMARY OF INVENTION

In various embodiments, the present invention comprises a system for documenting and coding diagnostic and interventional procedures for hospital and physician reimbursement, and automates the process of documenting and coding so that the two steps are unified into a singular activity. A computer-based system provides a graphical user interface allowing the physician to input details pertinent to the diagnostic and interventional procedures in an interactive manner. The computer program provides active guidance that enforces specification of details required to justify medical necessity of each performed procedure. The physician uses the computer program after completion of the actual procedure. Based on the physician's procedure entry, the program generates the resulting CPT (Current Procedural Terminology) codes and their accompanying documentation, thereby eliminating the opportunity for error. The program produces reports ready for submission for reimbursement.

Medical coding is based on a complex system of rules that depend on the particular anatomy of the patient (e.g., bypass grafts and anatomical variations), the combination of performed procedures, and medical necessity of the performed procedures. In one embodiment the system provides a number of anatomical charts that depict the blood vessels (i.e., arteries and veins) and organ systems. Furthermore, it allows the physician to specify the patient's existing bypass grafts and anatomical variations, which are then incorporated in the anatomical charts.

Using the graphical user interface of the computer program, the physician enters the diagnostic and interventional procedures, from access to closure and all procedure steps in-between, using point-and-click gestures in the anatomical charts. During the course of entering the procedures, the system provides active, context-based, guidance as to entry of medically necessary justification, so that each procedure step is directly documented in a compliant way.

After completion of procedure entry, the computer program generates reports that comply with documentation requirements necessary to code accurately, along with the appropriate CPT codes and modifiers for coding and billing purposes. Separate reports are generated for hospital and physician, including the appropriate codes and modifiers for each, for accurate and matching submission of claims to payers. The codes are automatically screened for NCCI (National Correct Coding Initiative) edits.

In an embodiment for endovascular procedures, for example, the diagnostic and interventional procedures that can be entered by the physician are percutaneous and open endovascular studies performed in the cardiac cath lab, angiography suite, operating room, or other similar locations in the hospital and outpatient setting. Diagnostic studies include angiography of blood vessels anywhere in the body, while interventions include techniques used to open or close abnormal vessels, heart chambers and other anatomic structures, interventional techniques to evaluate vessels further for diagnosis of pathology, and other therapies using these techniques.

Anatomical charts are interactive for accurate documentation of pathology evaluated and treatments performed. Variations in anatomy (congenital or post-surgical) impact the techniques used to perform the procedure and contribute to its complexity. The system features a wide range of predefined variations, as well as the ability for ad hoc inclusion of additional variations.

While the above examples are described in the context of endovascular-based procedures, the present invention can be used for procedures in other medical fields and disciplines.

The system may comprise a coding rules engine. The coding rules published by the AMA (American Medical Association), CMS (Centers for Medicare and Medicaid Services), MAC's (Medicare Administrative Contractor), and other societies requires very complex decision making for submission of accurate codes. These rules and guidelines are continually updated, along with new code creations and edits on an ongoing basis. The invention allows for continual updating based on these changes, so that hospitals and physicians always maintain compliant code submission.

Physician documentation drives correct medical coding. Without complete and accurate physician documentation, coding cannot be performed that would meet compliance review. In several exemplary embodiments, the present system creates a mechanism requiring the physician to document key components of procedures necessary for compliant submission of CPT codes for reimbursement.

Reporting options provided by the system include both physician and hospital report creation, including optional graphical depictions of areas evaluated and intervened on. The reporting optionally includes accurate CPT codes and modifiers based on the documentation. These reports may be signed and interface with the hospital and physician EHR (Electronic Health Record).

BRIEF DESCRIPTION OF THE DRAWINGS

FIG. 7 shows an example of a patient information screen.

FIG. 9 shows an example of a device list.

DETAILED DESCRIPTION OF EXEMPLARY EMBODIMENTS

Figure 1:
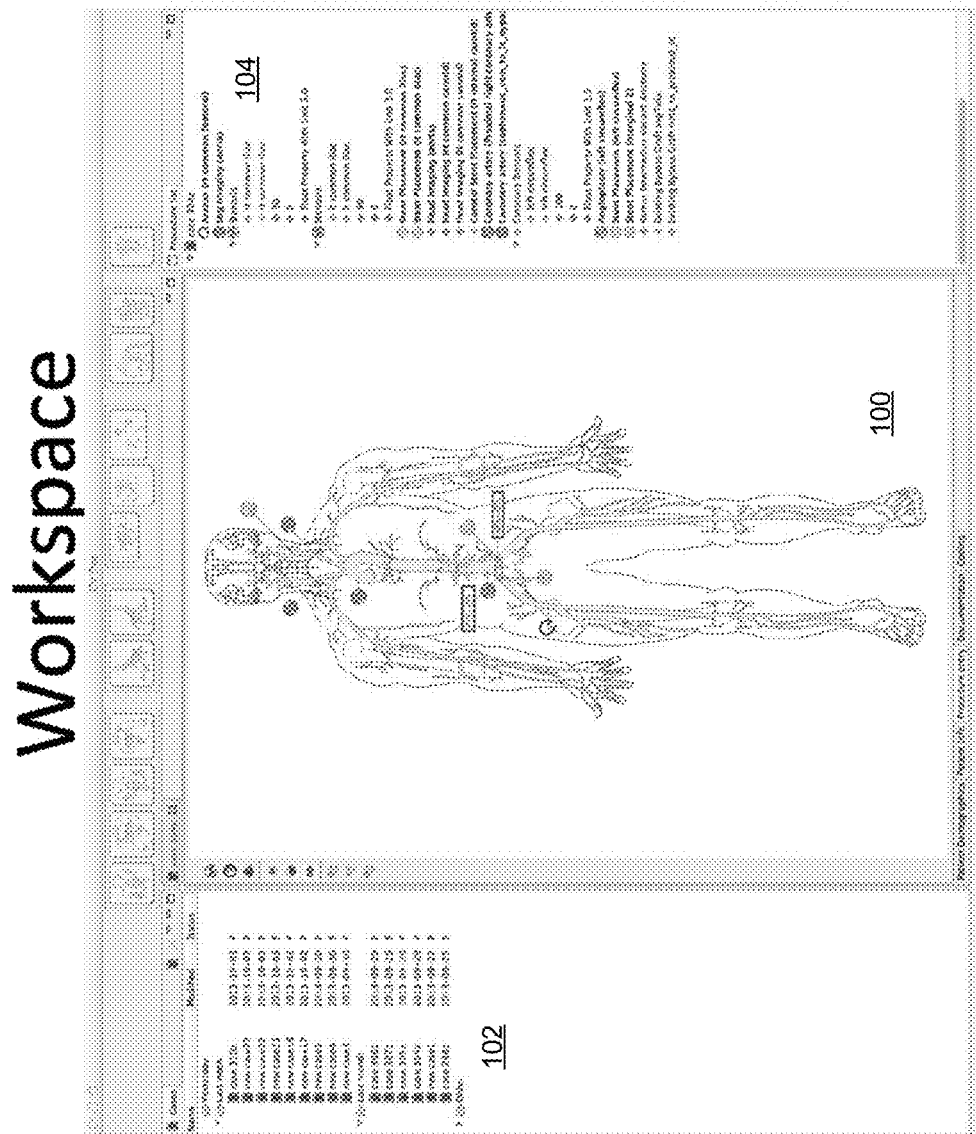
FIG. 1 shows an example of a workspace screen for a system in accordance with an embodiment of the present invention.

In several exemplary embodiments, the present invention automates the process of documenting and coding so that the two steps are unified into a singular activity. In one embodiment, the computer-based system provides a graphical user interface allowing the physician to input details pertinent to the diagnostic and interventional procedures in an interactive manner. The computer program provides active guidance that enforces specification of details required to justify medical necessity of each performed procedure. The physician uses the computer program after completion of the actual procedure. Based on the physician's procedure entry, the program generates the resulting CPT (Current Procedural Terminology) codes and their accompanying documentation, thereby eliminating the opportunity for error. The program produces reports ready for submission for reimbursement.

Medical coding is based on a complex system of rules that depend on the particular anatomy of the patient (e.g., bypass grafts and anatomical variations), the combination of performed procedures, and medical necessity of the performed procedures. As seen in FIGS. 1-13 and 22-29, in one embodiment the system provides a number of anatomical charts that depict the blood vessels (i.e., arteries and veins) and organ systems. Furthermore, it allows the physician to specify the patient's existing bypass grafts and anatomical variations, which are then incorporated in the anatomical charts.

The present invention thus eliminates the main sources of burden and cost in established workflow by generating accurate CPT codes as a result of standard physician structured data entry. This same data entry generates documentation to support the codes, which results in the codes from the hospital and the physician always being in agreement, as the system generates both.

In several embodiments, the system reduces all of the human arterial and vascular systems into an accurate nodal map. Nodes (i.e., all medically significant vessels) are based on the smallest areas of each vessel required to achieve accuracy of coding and documentation. The nodal maps includes variation for bypass grafts, and all relatively common (e.g., about 3% occurrence), naturally occurring human variant anatomy that affects coding accuracy and documentation.

A nodal map is potential unique for each individual patient. The map is entered into the system, and is stored in a database therein and communicated to the user (e.g., physician) in real time (the user may be remote). This ensures that the user is able to maintain an accurate human body map for each patient from case to case, and prevents forcing the user to enter similar information multiple times.

The system uses nodal searching and pathfinding techniques to find the best path from the access point of a case (e.g., where a catheter enters the body) to each procedure. These allows real time data to be applied to each procedure for a case. The system also creates custom "antegrade groups" of the body that create transient regions in system memory, where procedures inside the region must be differently than procedures outside the region. The pathfinding output is combined with a set of business rules (for catheter selectivity, antegrade vs. retrograde access, and vascular distribution grouping) to generate accurate catheter placement information, for example, which is used as a critical component to support proper CPT code generation.

Using the graphical user interface of the computer program, the physician enters the diagnostic and interventional procedures, from access to closure and all procedure steps in-between, using point-and-click gestures in the anatomical charts. During the course of entering the procedures, the system provides active, context-based, guidance as to entry of medically necessary justification, so that each procedure step is directly documented in a compliant way.

Figure 2:
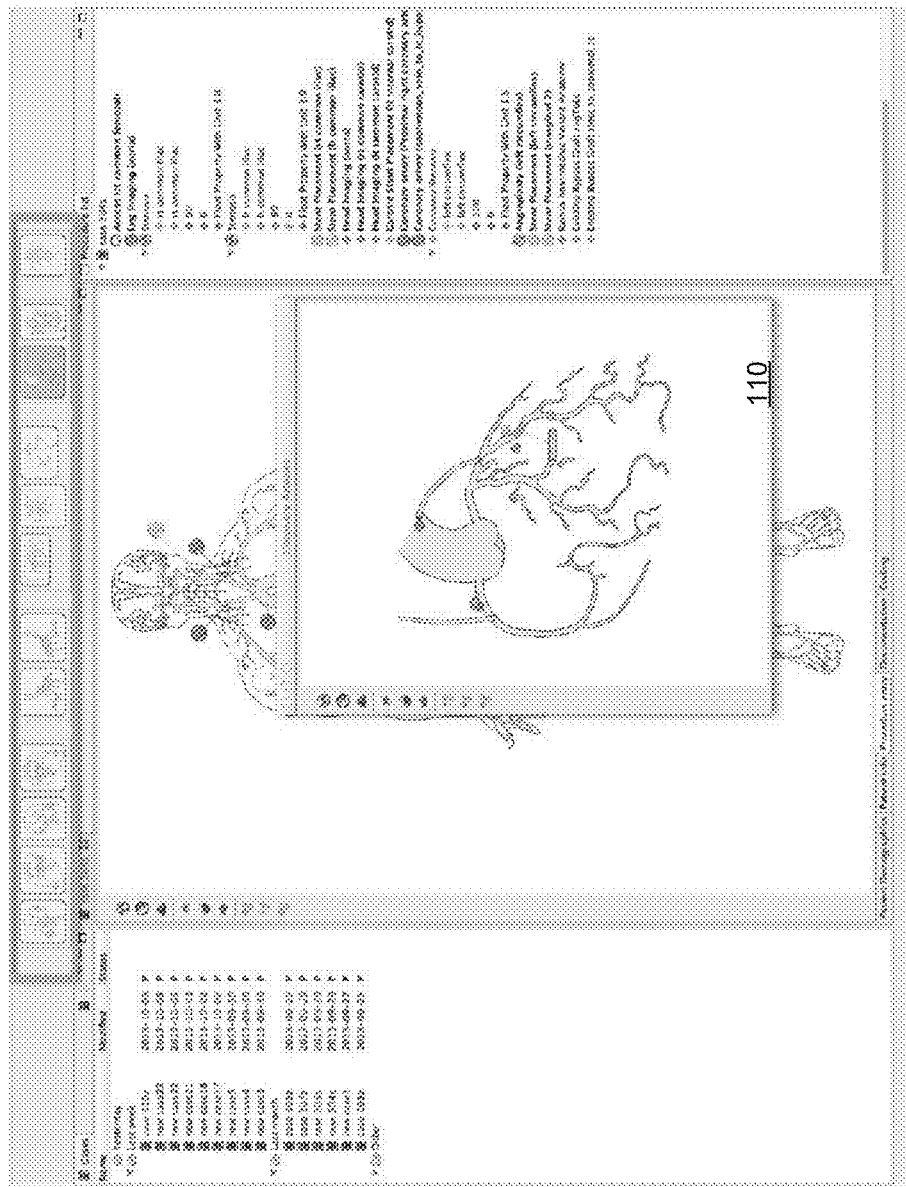
FIG. 2 shows an example of chart window.
Figure 3:
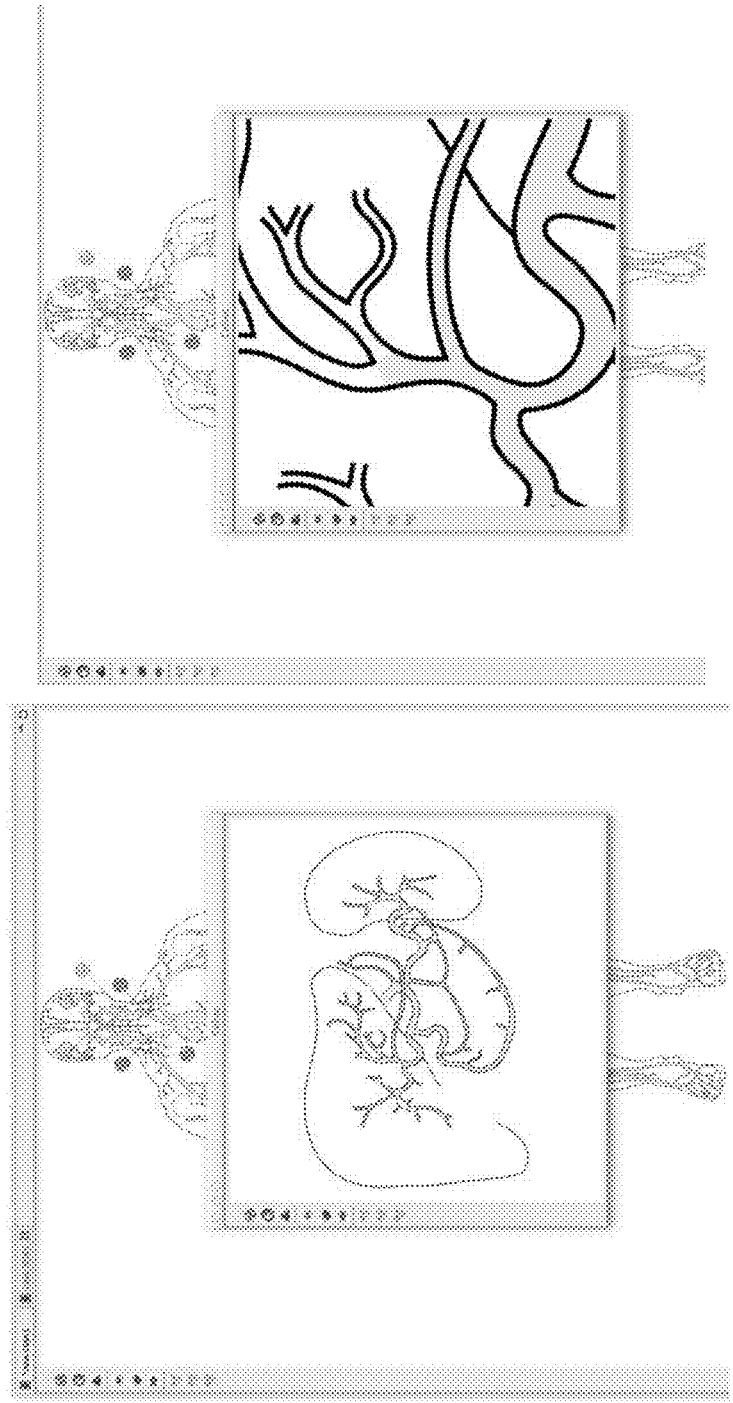
FIG. 3 shows an example of a magnification window.
Figure 4:
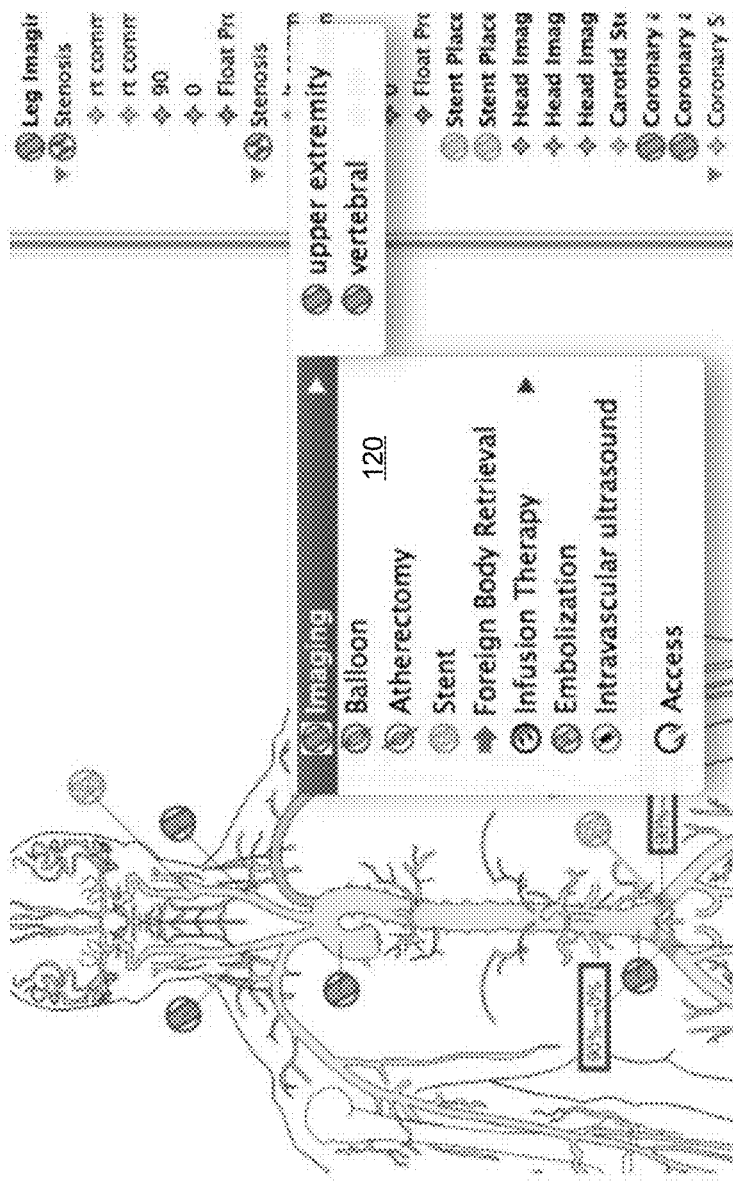
FIG. 4 shows an example of a procedure input screen.

FIG. 1 shows an example of a workspace screen with a nodal map 100 of the patient. The nodal map is for a particular case, which may be selected from the case list 102 on the left of the screen. The procedure list 104 for this particular case is seen on the right of the screen. The physician (or other user) may click on a particular part of the nodal map, which causes that part (in this case, coronary arteries) to expand into a separate window 110, as seen in FIG. 2. Alternatively, the view can expand directly without opening a separate window. The user can then zoom further into a magnified view of details in that window or view, as seen FIG. 3. From the main nodal map, or any window showing portions thereof, the user can then specify which procedures were performed at particular locations. In the embodiment shown in FIG. 4, the user has clicked on a particular location, and is presented a menu of procedure options (including devices) 120 from which to select. Each option may have sub-options or sub-menus. Procedures or devices already input may be shown on the nodal map by icons or other indications.

Figure 5:
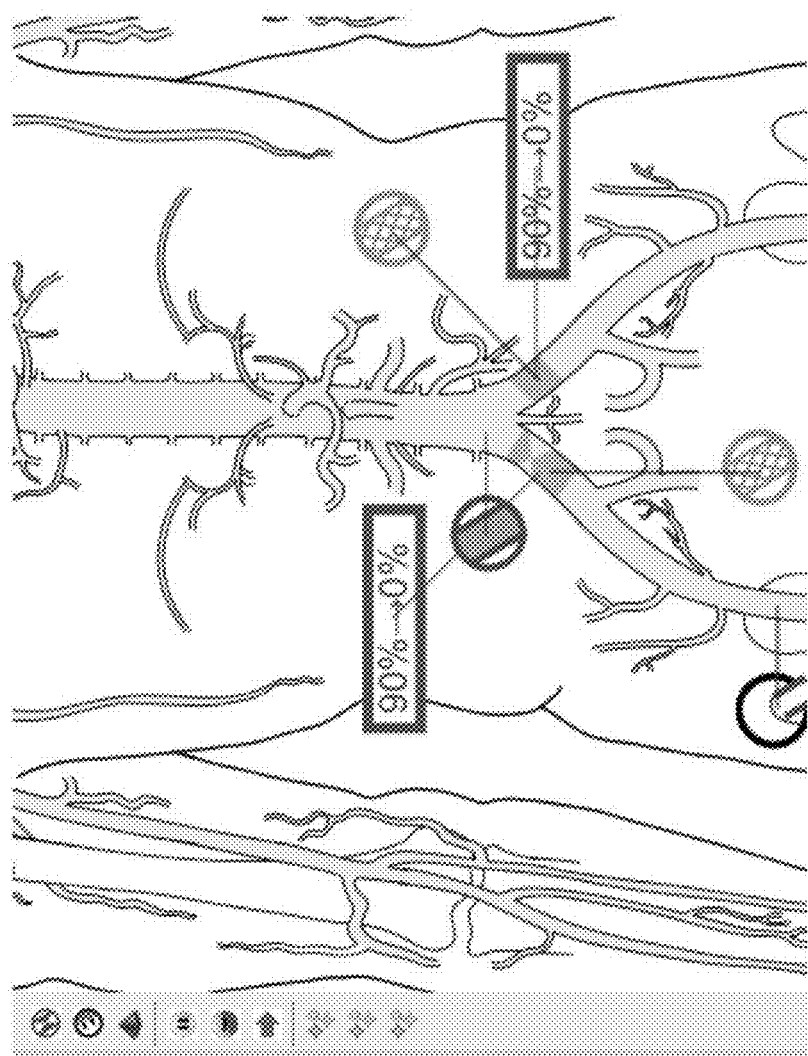
FIG. 5 shows an example of an interactive drawing screen.

Conditions also may be shown or drawn interactively on the nodal map by the user. FIG. 5 shows an example of the drawing of lesions on a magnified area of the nodal map.

Figure 6:
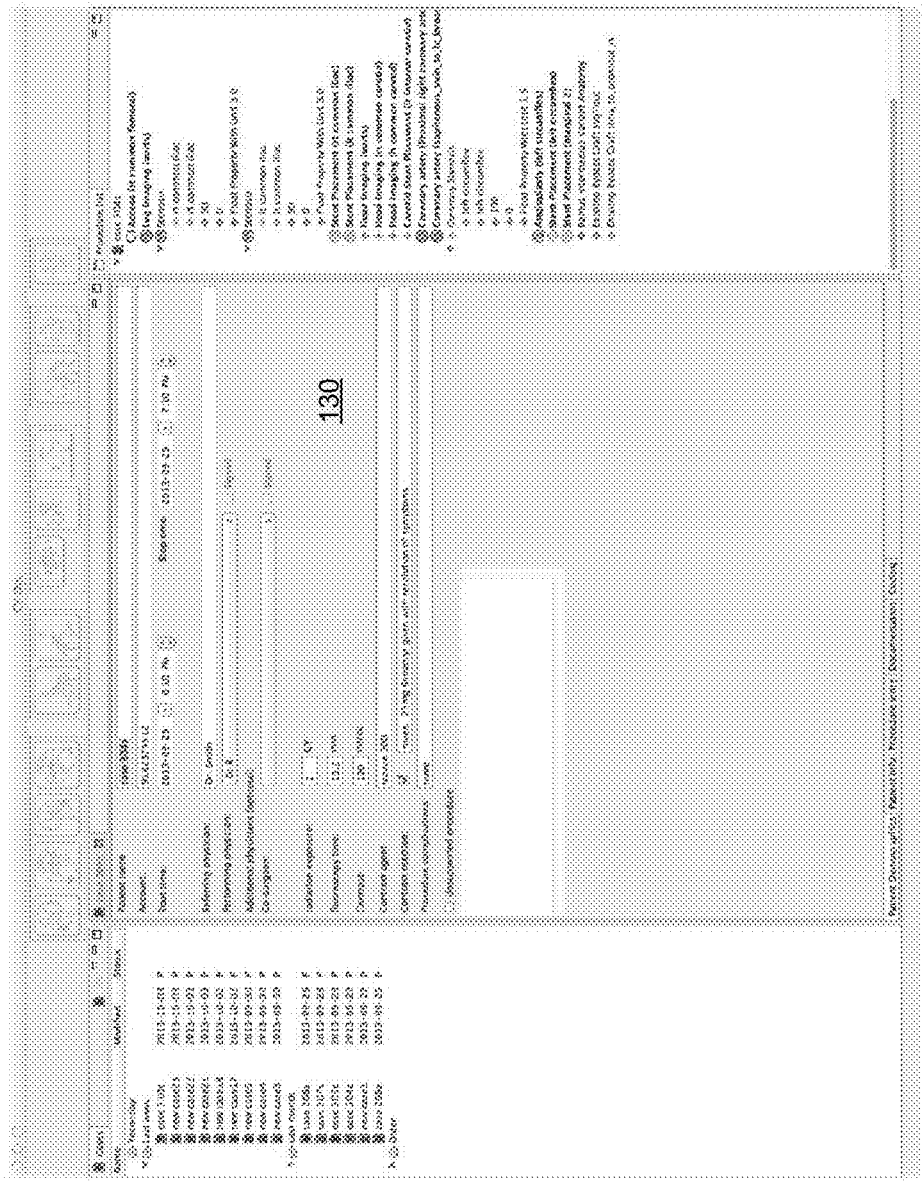
FIG. 6 shows an example of a patient demographics screen.
Figure 7:
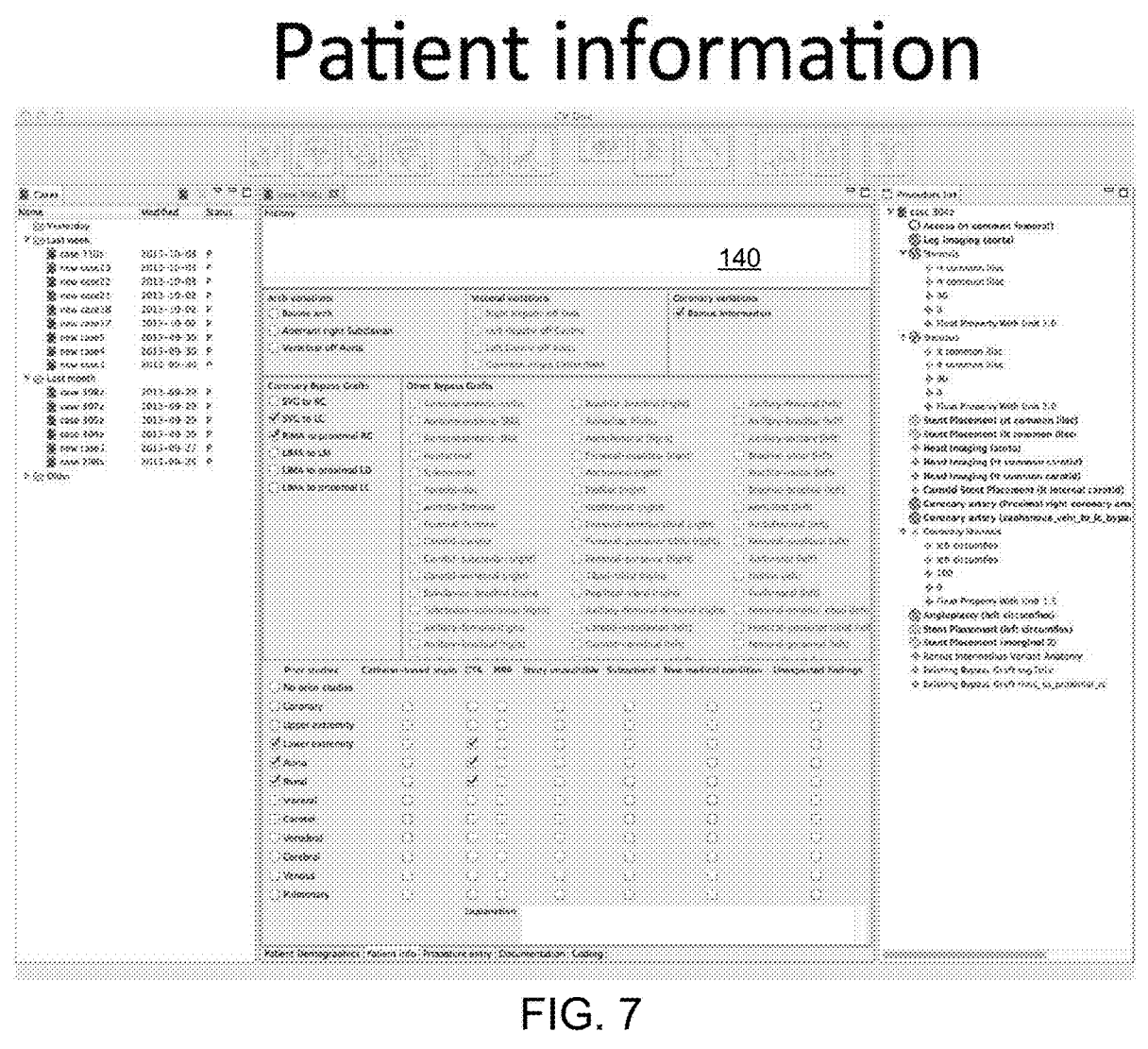

The user also is prompted to enter demographical information 130 about the patient and procedure, as seen in FIG. 6. This includes, but is not limited to, patient name, patient account, start date and time, stop date and time, referring physician, performing physician, additional physicians (co-surgeons), radiation exposure, fluoroscopy time, contrast, contrast agent, contrast reaction, procedure complications, and whether the procedure is unsupported. This information may be automatically and interoperatively loaded from the Electronic Health Record (EHR) for the individual. Similarly, other patient information 140 may be entered or loaded, as seen in FIG. 7. This includes, but is not limited to, patient history, arch variations, visceral variations, coronary variations, coronary bypass grafts, other bypass grafts, and prior studies.

Figure 8:
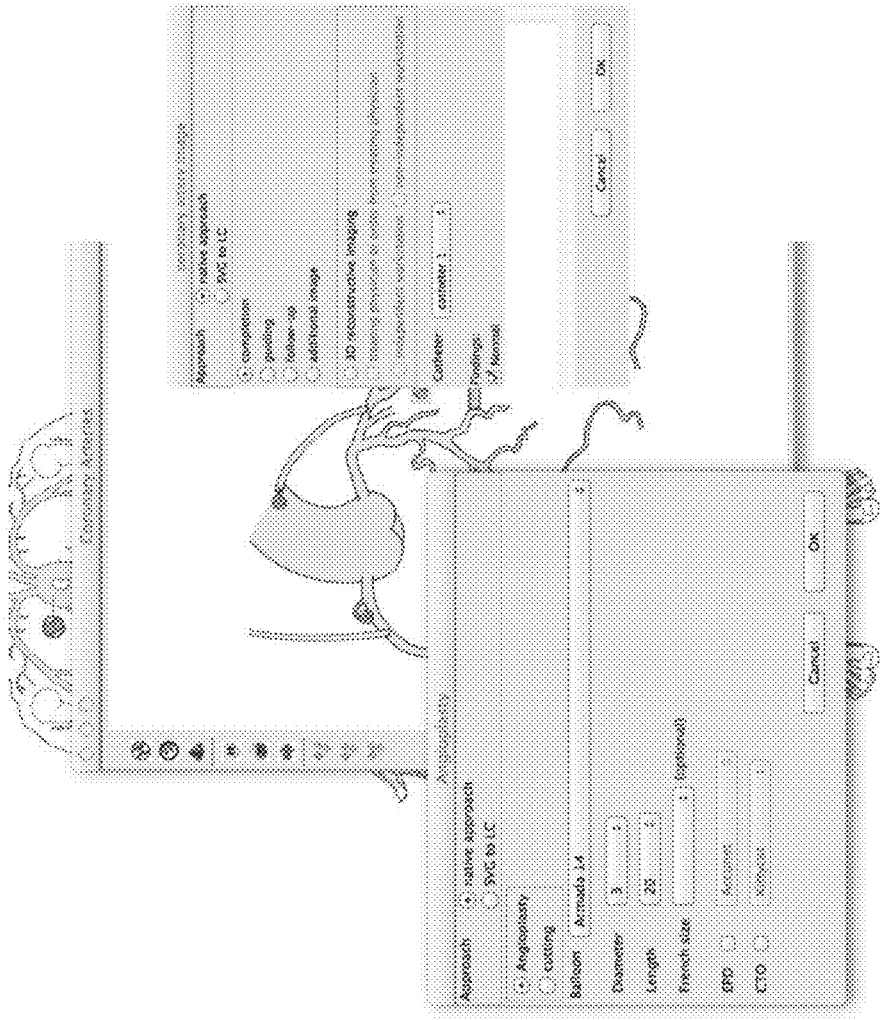
FIG. 8 shows an example of dialog windows.
Figure 9:
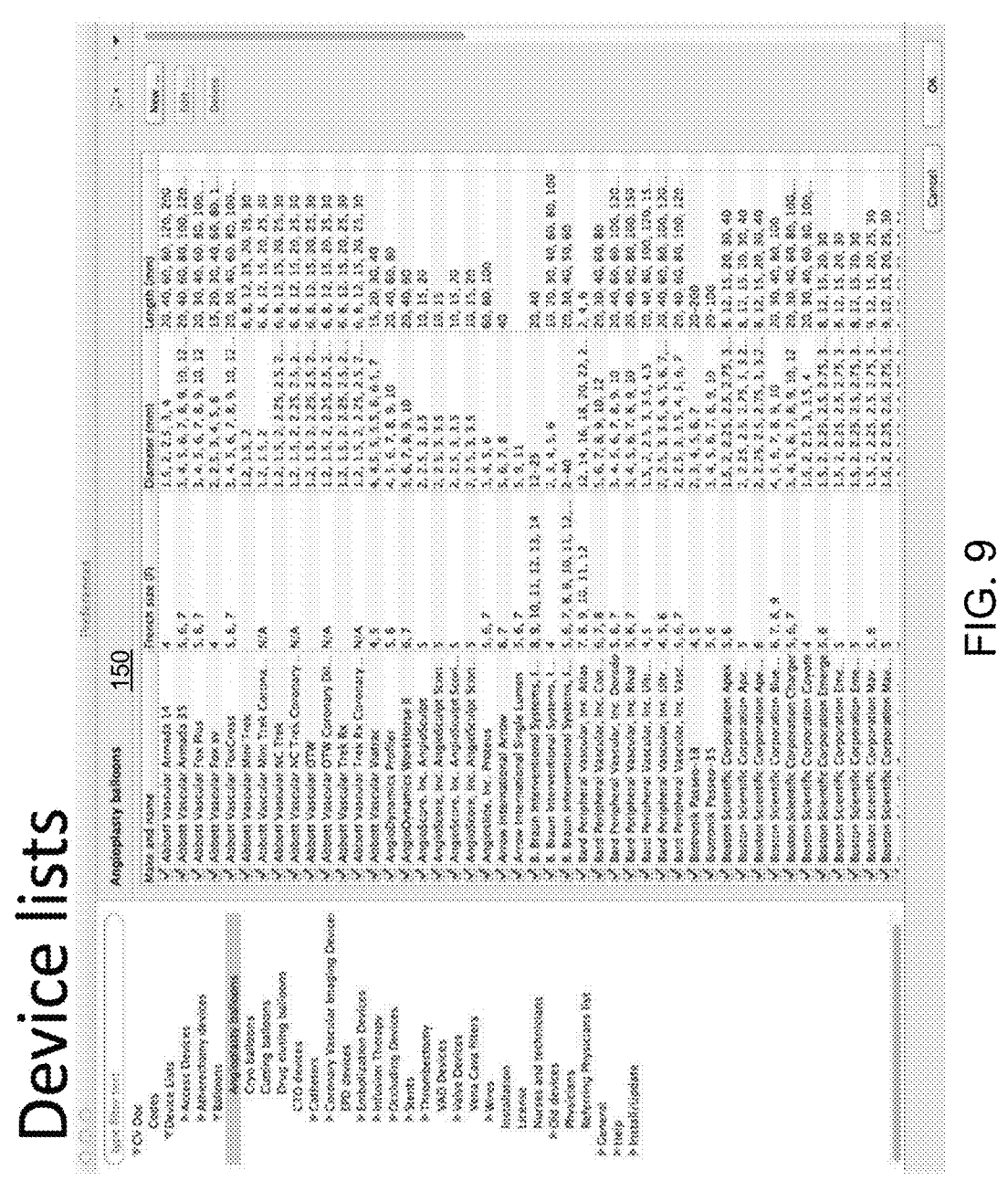

During the course of entering the procedures, as mentioned above, the system provides active, context-based, guidance as to entry of medically necessary justification, as seen in FIG. 8, so that each procedure step is directly documented in a compliant way. FIG. 9 shows an exemplary list of devices 150 for the user to choose from (in this case, angioplasty balloons). The information can be very detailed, including manufacturer and sizes. Alternatively, the user may be presented with a list of only those devices actually used in the procedure from the hemodynamic system (utilized inventory system) associated with the operation, and interoperatively loaded in the present system.

Figure 10:
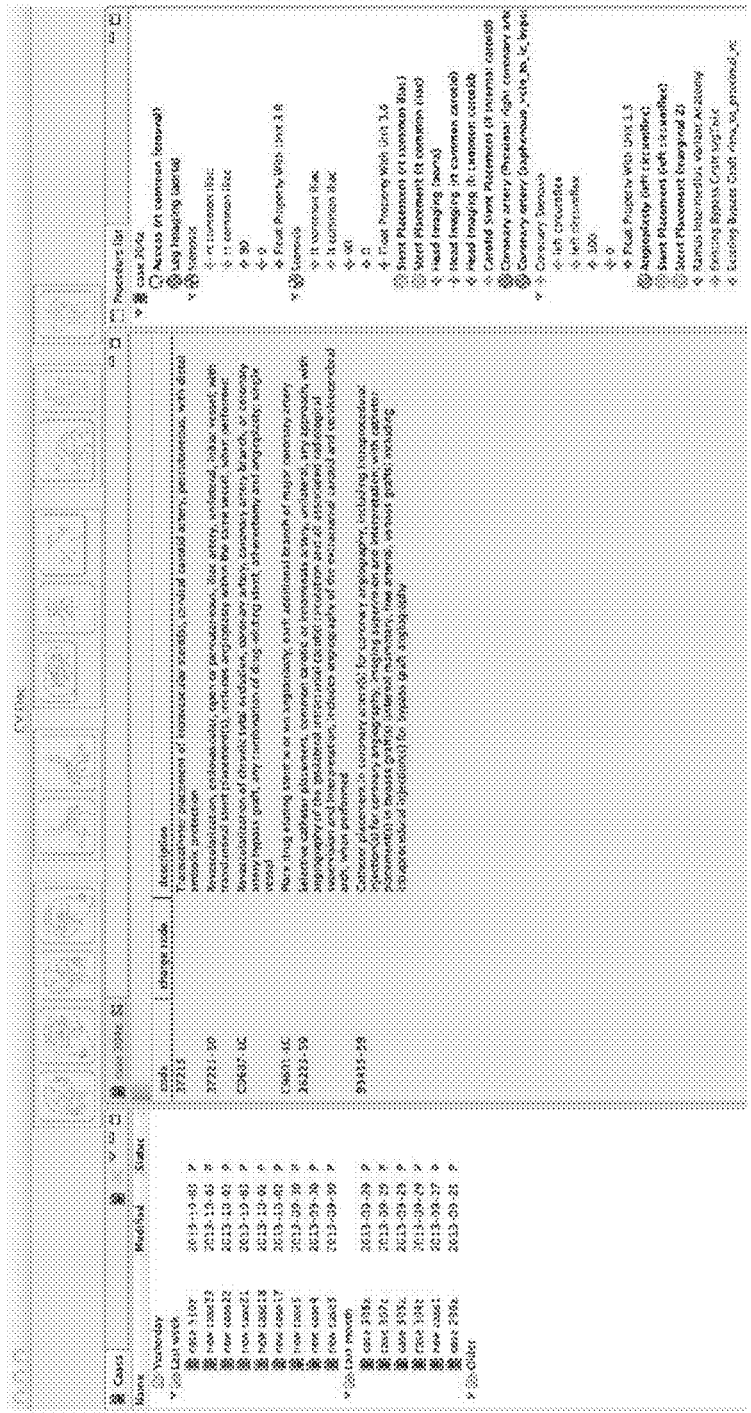
FIG. 10 shows an example of a generated CPT codes list.
Figure 11:
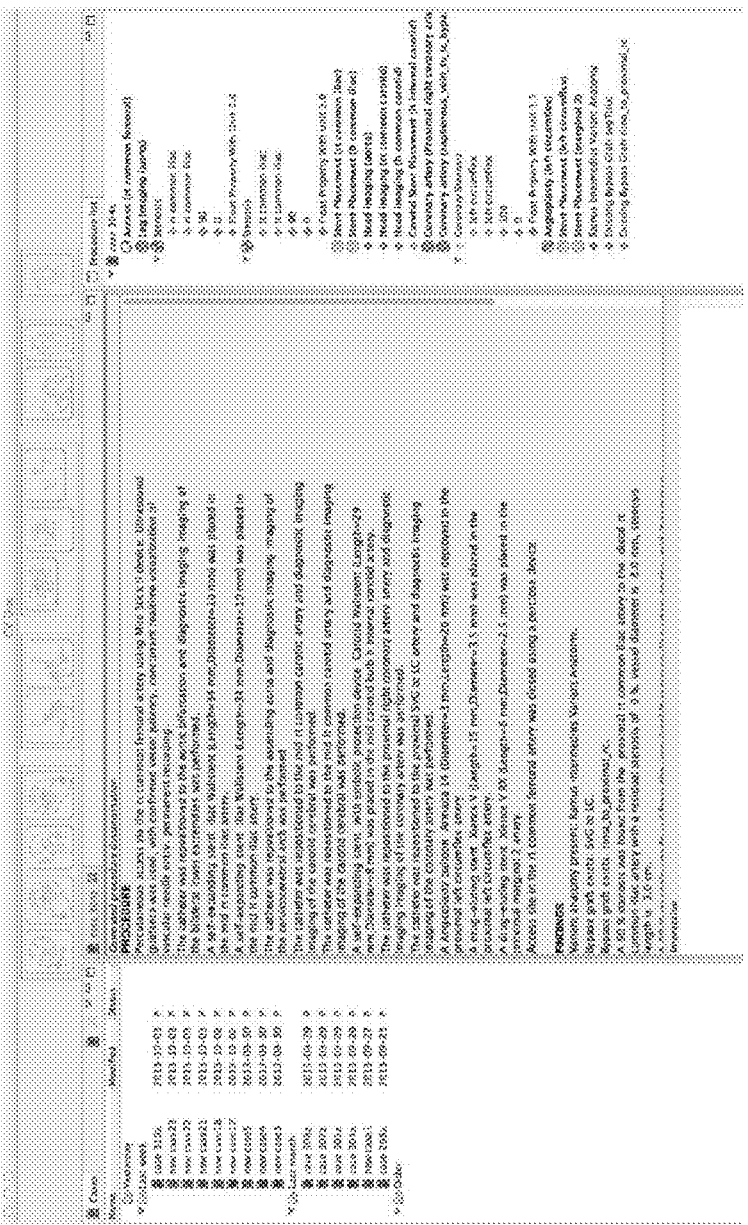
FIG. 11 shows an example of a generated supporting documentation screen.
Figure 12:
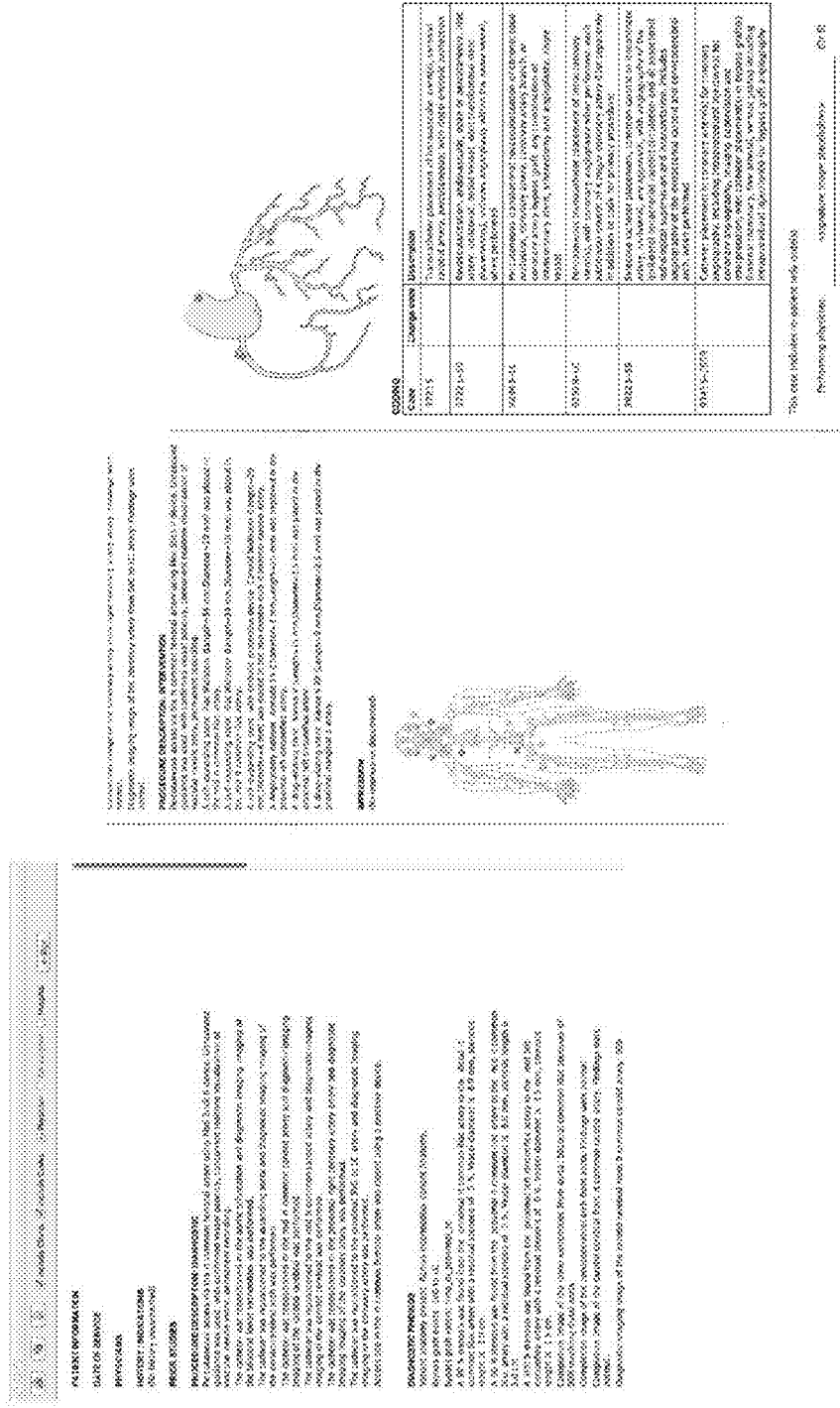
FIG. 12 shows an example of a reports screen.
Figure 13:
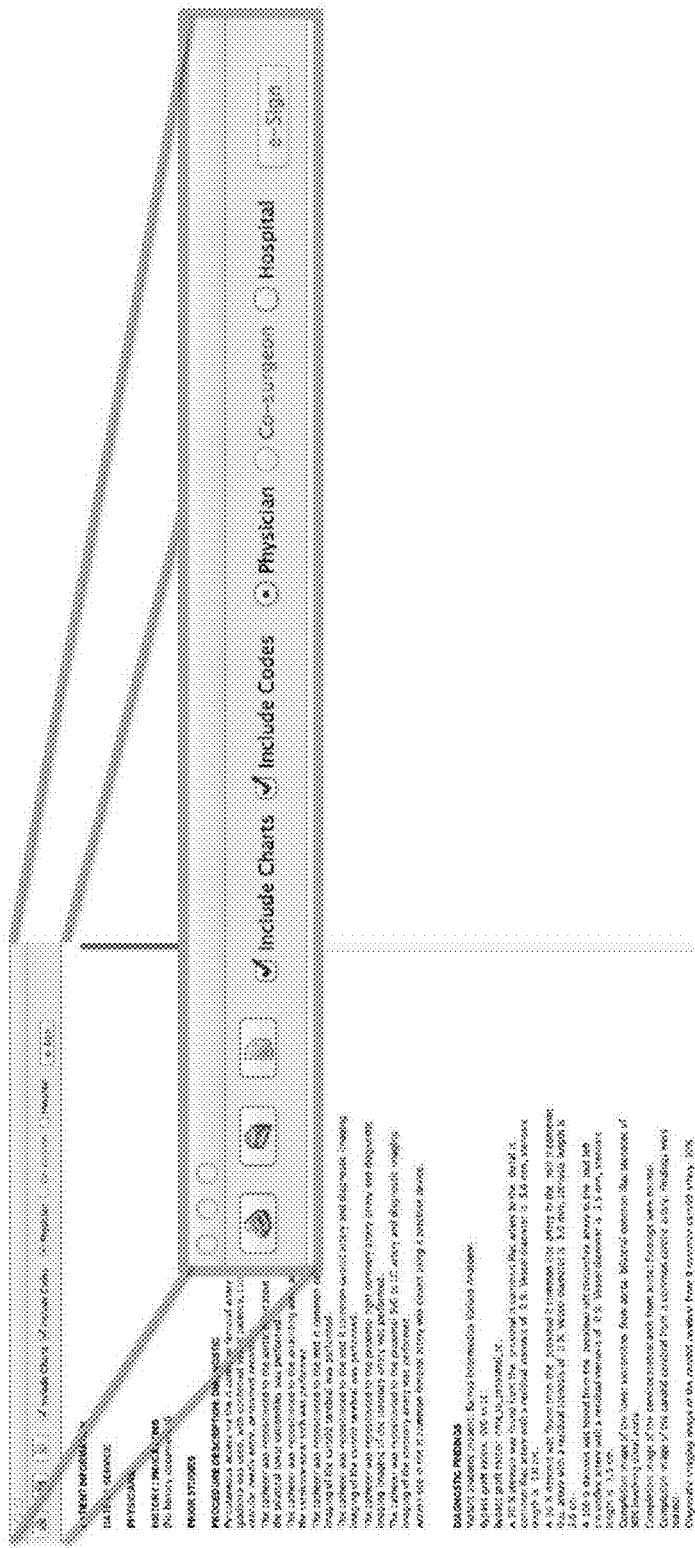
FIG. 13 shows an example of a reports destination window.

After completion of procedure entry, the computer program generates appropriate CPT codes and documentation, as seen in FIGS. 10 and 11. It also generates reports, as seen in FIG. 12, that comply with documentation requirements necessary to code accurately, along with the appropriate CPT codes and modifiers for coding and billing purposes. Separate reports are generated for hospital and physician, including the appropriate codes and modifiers for each, for accurate and matching submission of claims to payers. The user can specify report destinations and options, as seen in FIG. 13. The codes are automatically screened for NCCI (National Correct Coding Initiative) edits.

Alternative embodiments of the workspace and input screens are shown in FIGS. 22-29.

In an embodiment for endovascular procedures, for example, the diagnostic and interventional procedures that can be entered by the physician are percutaneous and open endovascular studies performed in the cardiac cath lab, angiography suite, operating room, or other similar locations in the hospital and outpatient setting. Diagnostic studies include angiography of blood vessels anywhere in the body, while interventions include techniques used to open or close abnormal vessels, heart chambers and other anatomic structures, interventional techniques to evaluate vessels further for diagnosis of pathology, and other therapies using these techniques.

Anatomical charts are interactive for accurate documentation of pathology evaluated and treatments performed. Variations in anatomy (congenital or post-surgical) impact the techniques used to perform the procedure and contribute to its complexity. The system features a wide range of predefined variations, as well as the ability for ad hoc inclusion of additional variations.

While the above examples are described in the context of endovascular-based procedures, the present invention can be used for procedures in other medical fields and disciplines.

The system may comprise a coding rules engine. The coding rules published by the AMA (American Medical Association), CMS (Centers for Medicare and Medicaid Services), MAC's (Medicare Administrative Contractor), and other societies requires very complex decision making for submission of accurate codes. These rules and guidelines are continually updated, along with new code creations and edits on an ongoing basis. The invention allows for continual updating based on these changes, so that hospitals and physicians always maintain compliant code submission.

Physician documentation drives correct medical coding. Without complete and accurate physician documentation, coding cannot be performed that would meet compliance review. In several exemplary embodiments, the present system creates a mechanism requiring the physician to document key components of procedures necessary for compliant submission of CPT codes for reimbursement.

Reporting options provided by the system include both physician and hospital report creation, including optional graphical depictions of areas evaluated and intervened on. The reporting optionally includes accurate CPT codes and modifiers based on the documentation. These reports will be signed and interface with the hospital and physician EHR (Electronic Health Record).

Figure 14:
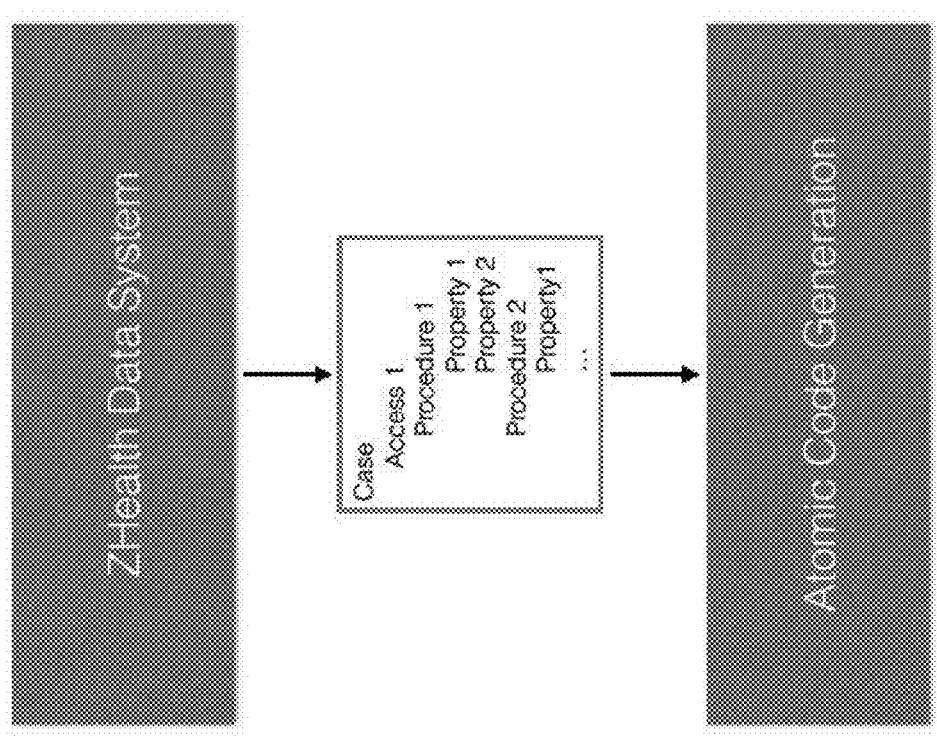
FIG. 14 shows a diagram of system database output.

In several embodiments, the coding engine takes a structured data set that describes the sequence and details of the steps performed by the physician during the course of the cases (i.e., procedures), and converts them into 100% correct CPT codes (including any NCCI modifiers). The system accurately handles existing codes, and easily encompasses and integrates new codes. The method for performing this conversion, in one embodiment, comprises the following steps:

1. Receive and store case and procedure data (see FIG. 14). This information is generated as described above, and is stored in one or more system databases. In this example, a case has access sites (i.e., places where the catheter has entered the body). Access sites have procedures associated with them (i.e., procedures done from that access site). Procedures have properties (i.e., details of the individual billable things the physician did while performing that procedure).

Figure 15:
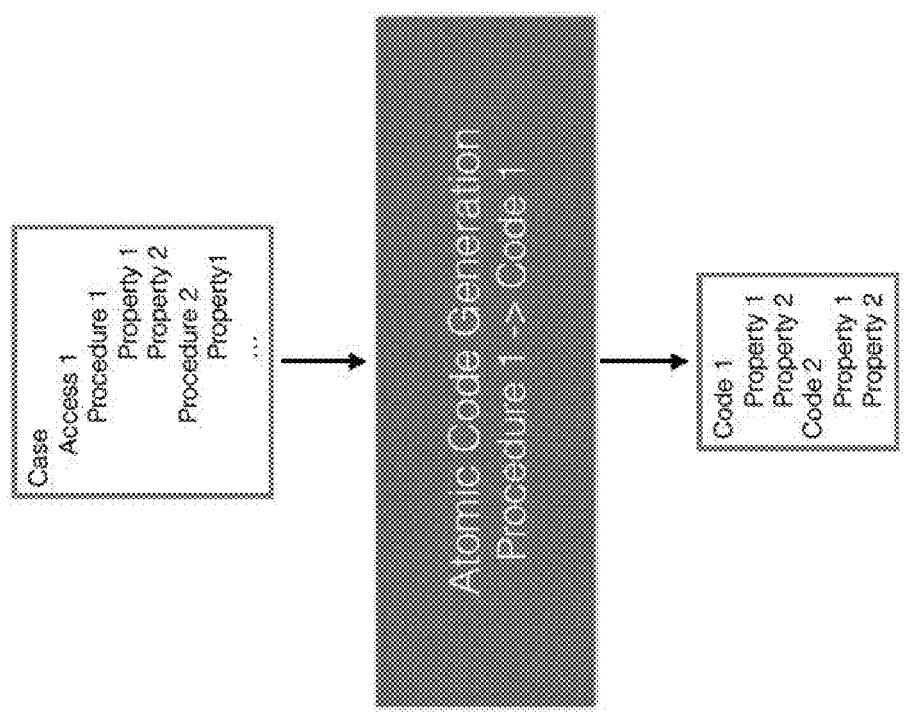
FIG. 15 shows a diagram of atomic code generation.

2. Generate atomic code for the case and procedure data (see FIG. 15). Atomic codes are generated for each procedure. The atomic code map looks at what was done, where it was done, and the circumstances of the individual procedure. This step analyzes procedures individually without additional context required for proper coding. Multiple atomic codes are possible for each procedure. Atomic codes retain the properties of the procedures that produced them. The output of the atomic code step is at least 1-to-1, so there are as many codes as there are procedures, at a minimum.

Figure 16:
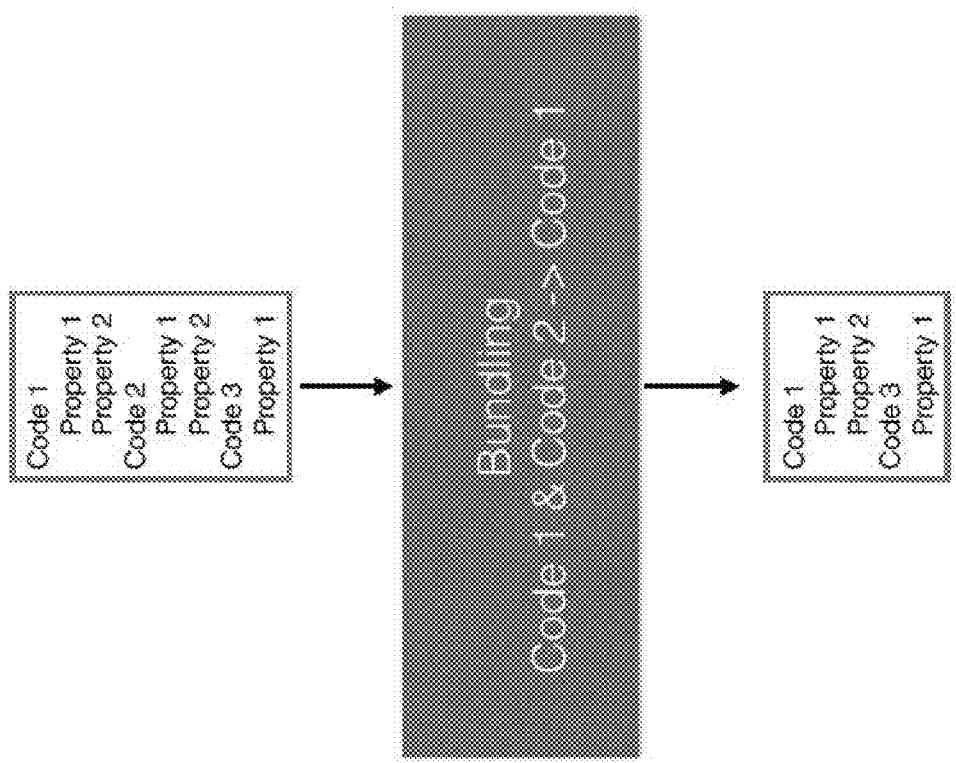
FIG. 16 shows a diagram of a bundling procedure.

3. Bundle codes together based on discrete logic rules and procedure location (see FIG. 16). A single CPT code can apply to multiple procedures performed in a certain area of the body. Bundling looks across and analyzes the entire case, and always rolls codes up to an already existing code.

Figure 17:
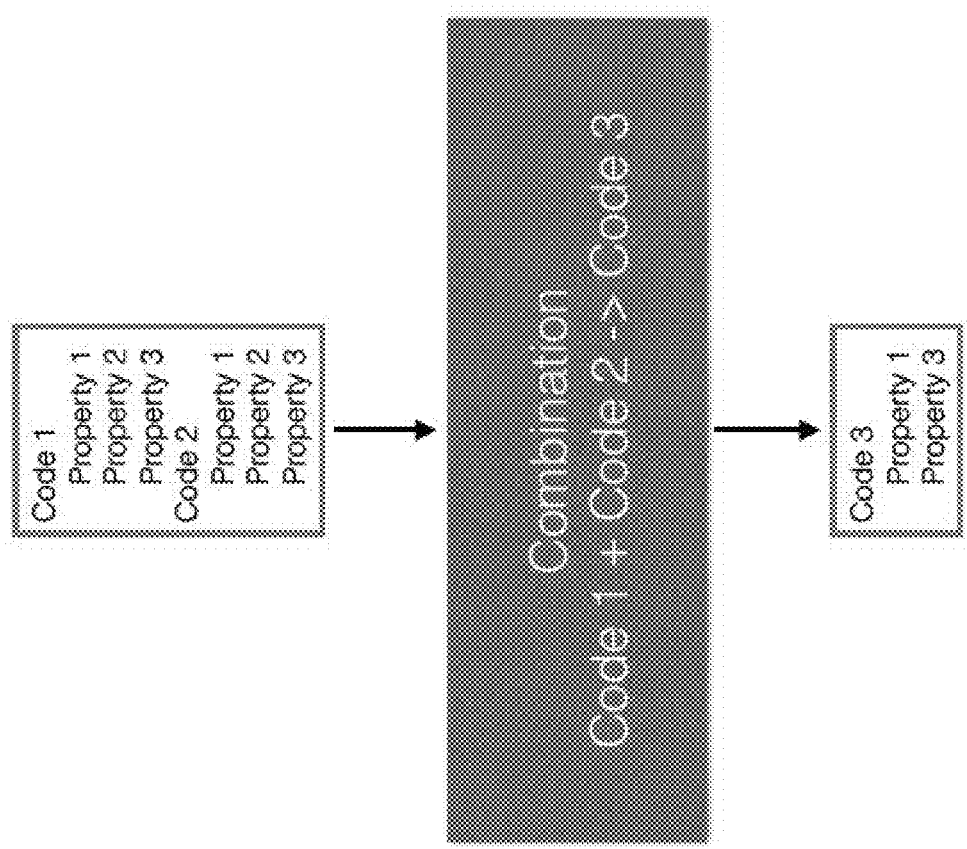
FIG. 17 shows a diagram of a code combining procedure.

4. Combine multiple codes into a single new code (see FIG. 17). Combining is the act of combining two different codes into a new code. The new code may or may not be able to take on the properties of both of the old codes. In one embodiment, only when properties are identical in the old codes do they stay attached to the new code.

Figure 18:
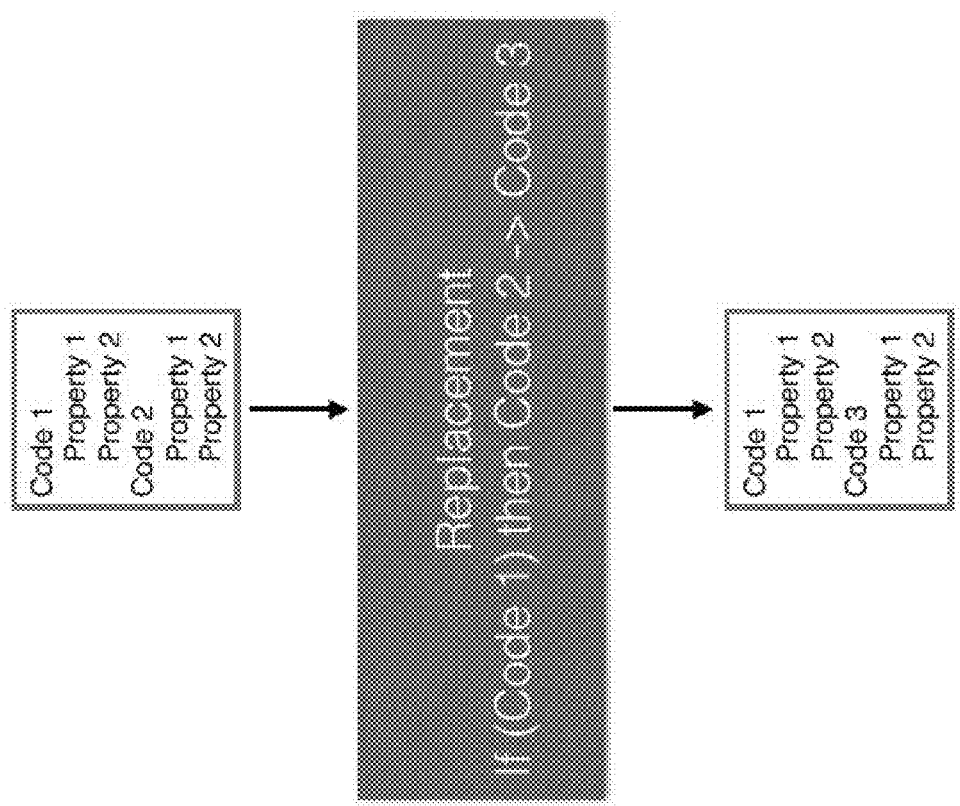
FIG. 18 shows a diagram of a code replacement procedure.

5. Replace a code with a new code due to contextual logic of the other case elements (see FIG. 18). Replacement is the changing of a code to a different code without affecting any other codes in the case. This can be used, for example, for additional codes that are required for subsequent instances of a procedure. For example, the first stent in a coronary distribution may be code 92928, while all subsequent stents in the same distribution receive replacement code 92929.

Figure 19:
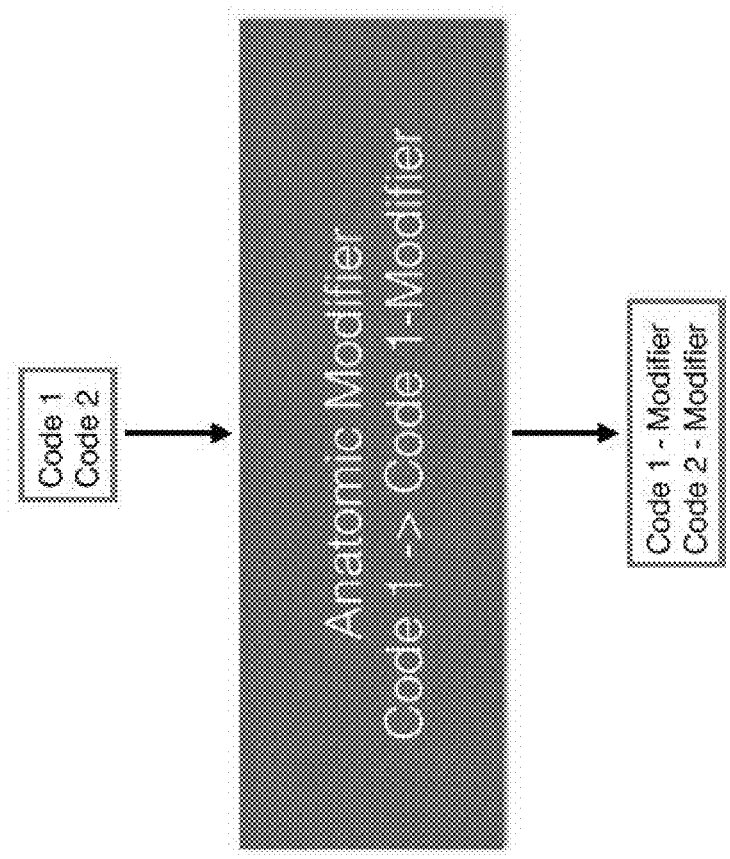
FIG. 19 shows a diagram of anatomic modifications.

6. Add anatomic modifiers based on the physical location of each code (see FIG. 19). Some payors or facilities desire (or require) modifiers placed on a code to indicate where in the body the procedure was performed. These modifiers typically are alphanumeric characters added to the base code. They are purely additive, and do not affect the base code. For example, 92928 is modified to become 92928-RC when performed in the Right Coronary.

7. Add additional modifiers based on Boolean, combinational, and contextual logic. These are similar to anatomic modifiers, but not based physical location.

8. Perform NCCI compliance scrubbing. NCCI code conformity is required by Medicare, among other entities. The system ensures that the submitted codes conform to NCCI so that they do not get immediately rejected. The system removes codes that are unbillable (typically in combination with each other), or adds a "reduced payment" modifier (i.e., −59) where appropriate.

Figure 20:
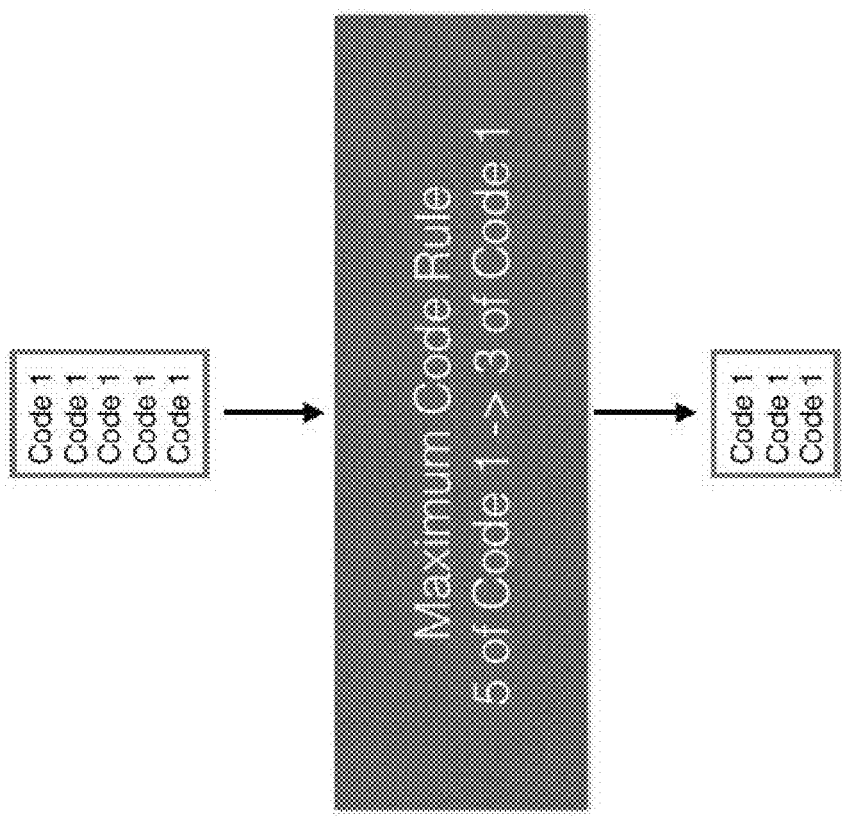
FIG. 20 shows a diagram of the maximum code rule procedure.

9. Apply maximum code rule (see FIG. 20). There are hard limits to the number of codes, or the number of a particular code, that can be submitted in a given area of the body, with the maximum number of codes depending on the location and the exact codes in issue. This step removes codes from the bill that are in addition to or in excess of the maximum billable amount. It does not affect the documentation that those procedures were performed.

Figure 21:
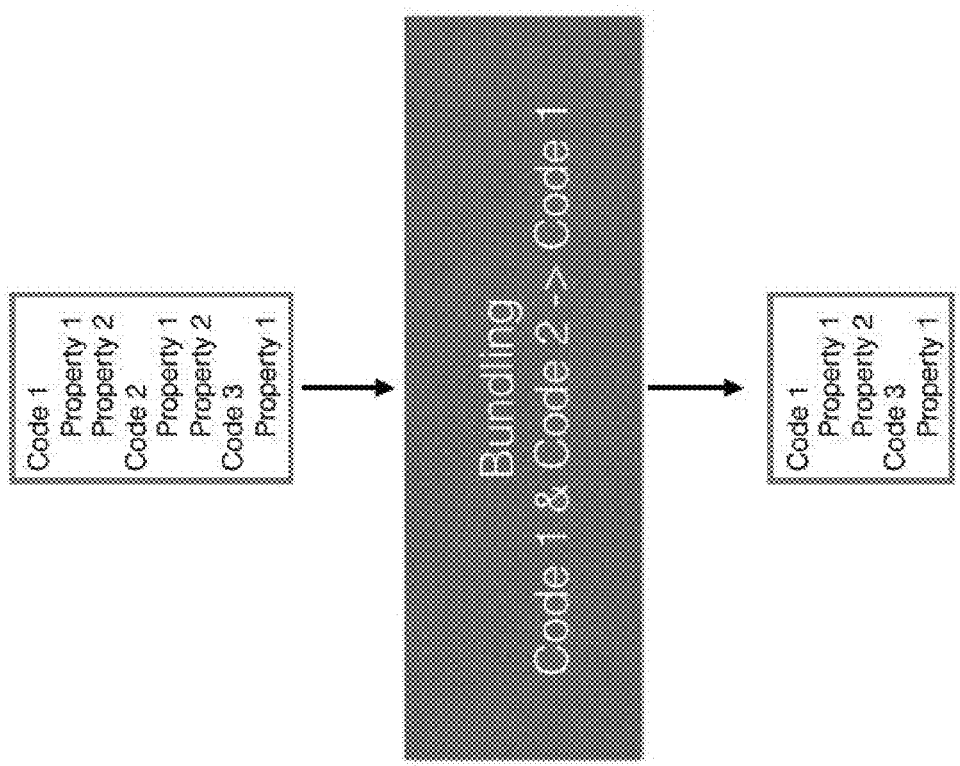
FIG. 21 shows a diagram of the final bundling procedure.
Figure 22:
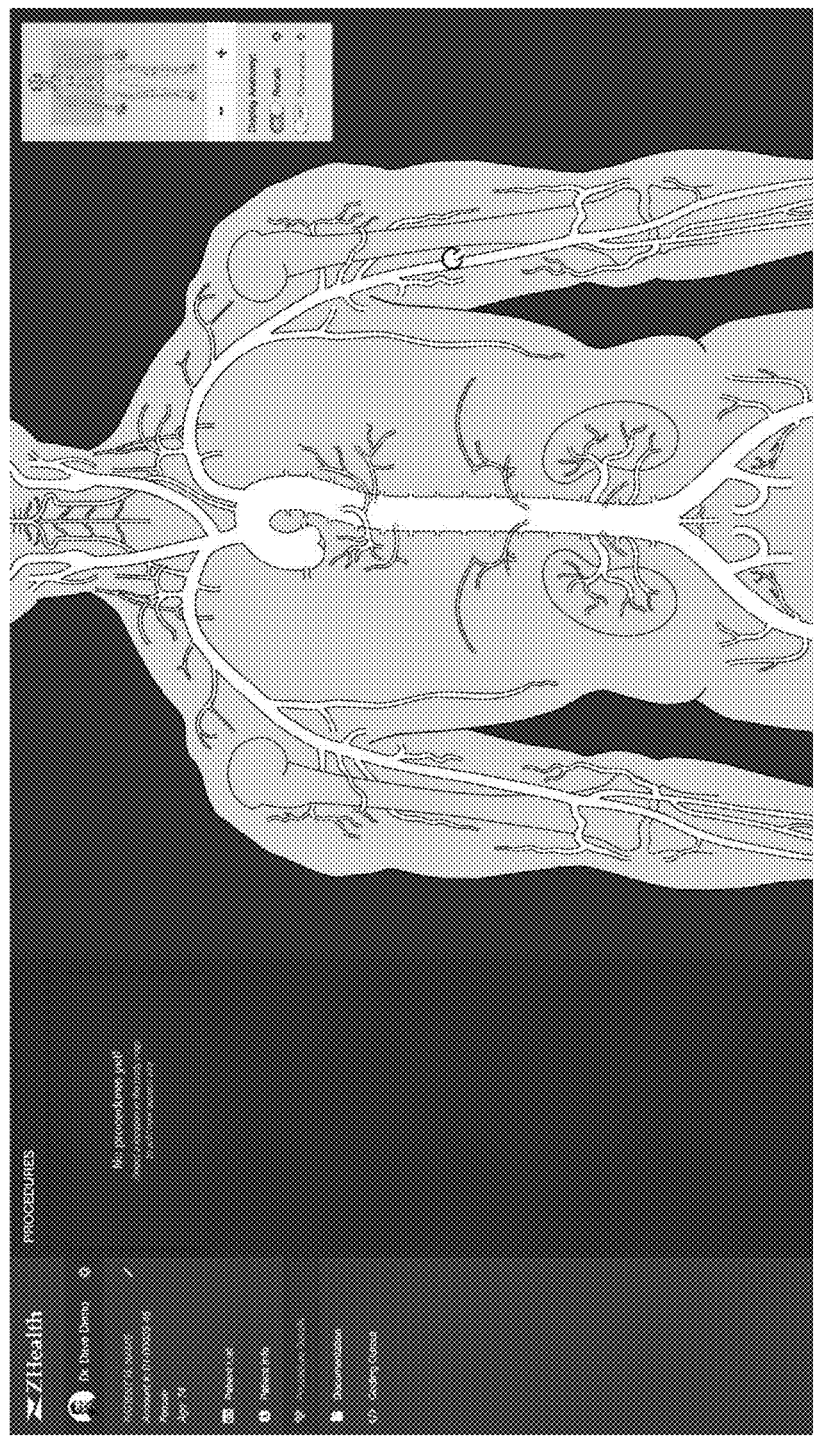
FIG. 22 shows another example of a workspace screen with no access points yet selected.
Figure 23:
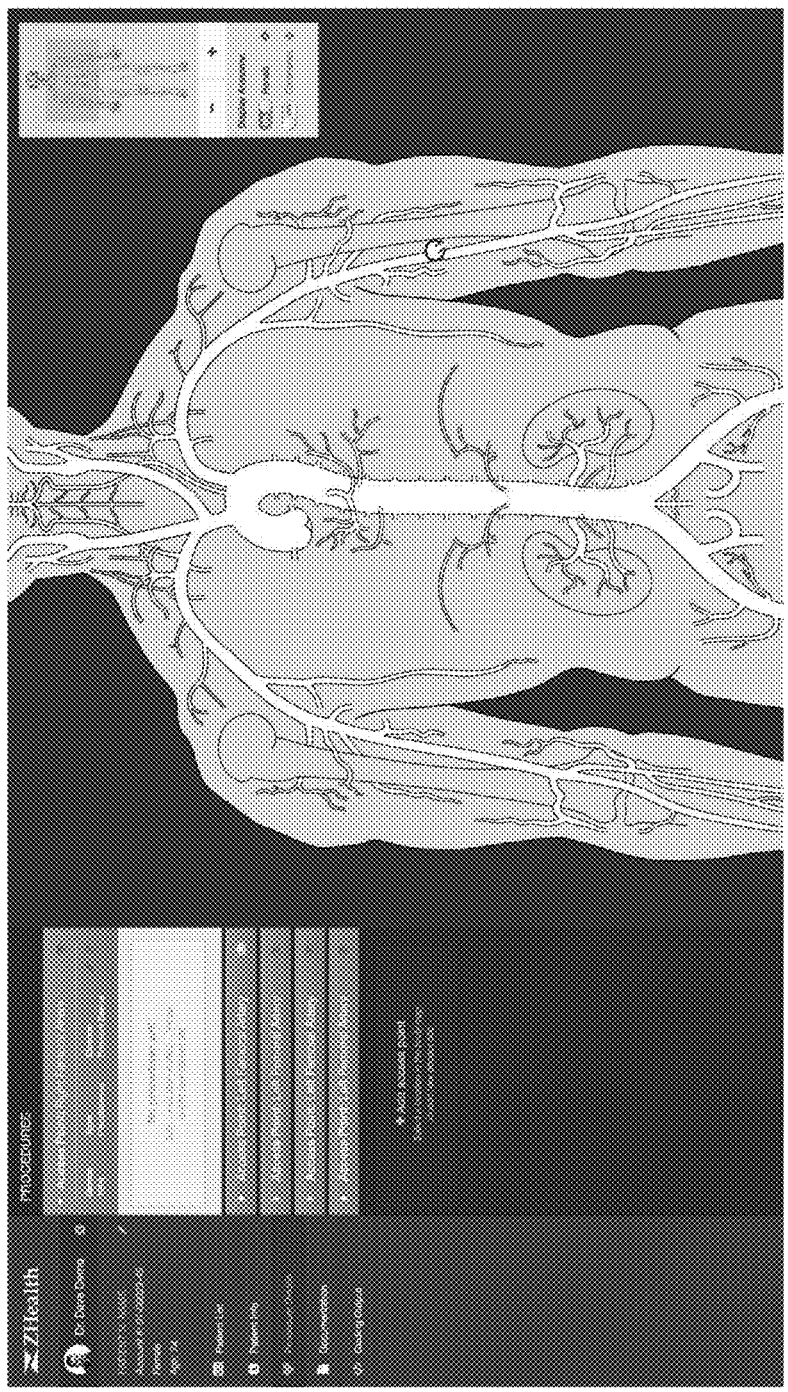
FIG. 23 shows an example of a workspace screen with access points selected, but no procedures selected.
Figure 24:
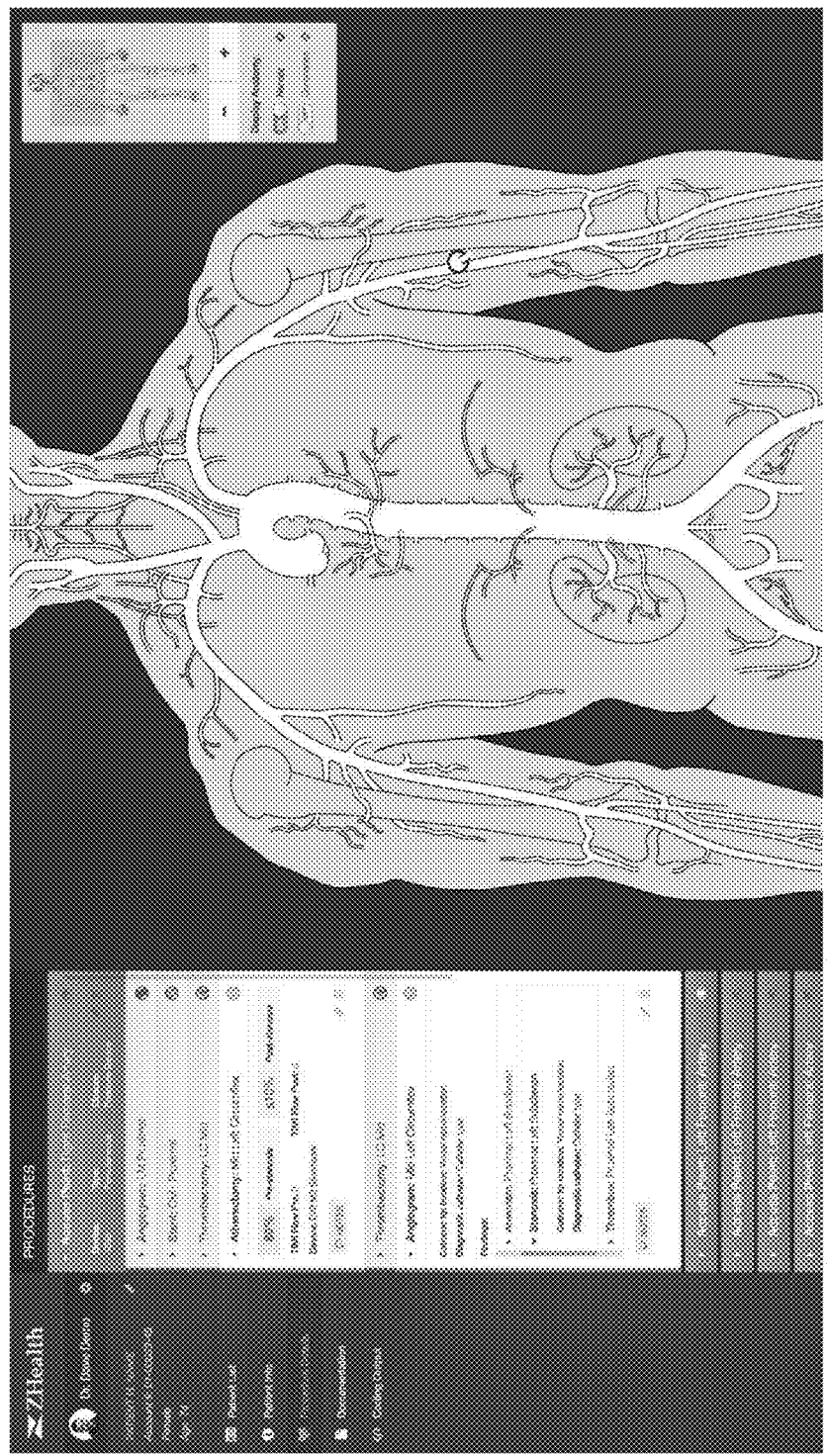
FIG. 24 shows an example of a workspace screen with access points and procedures selected.
Figure 25:
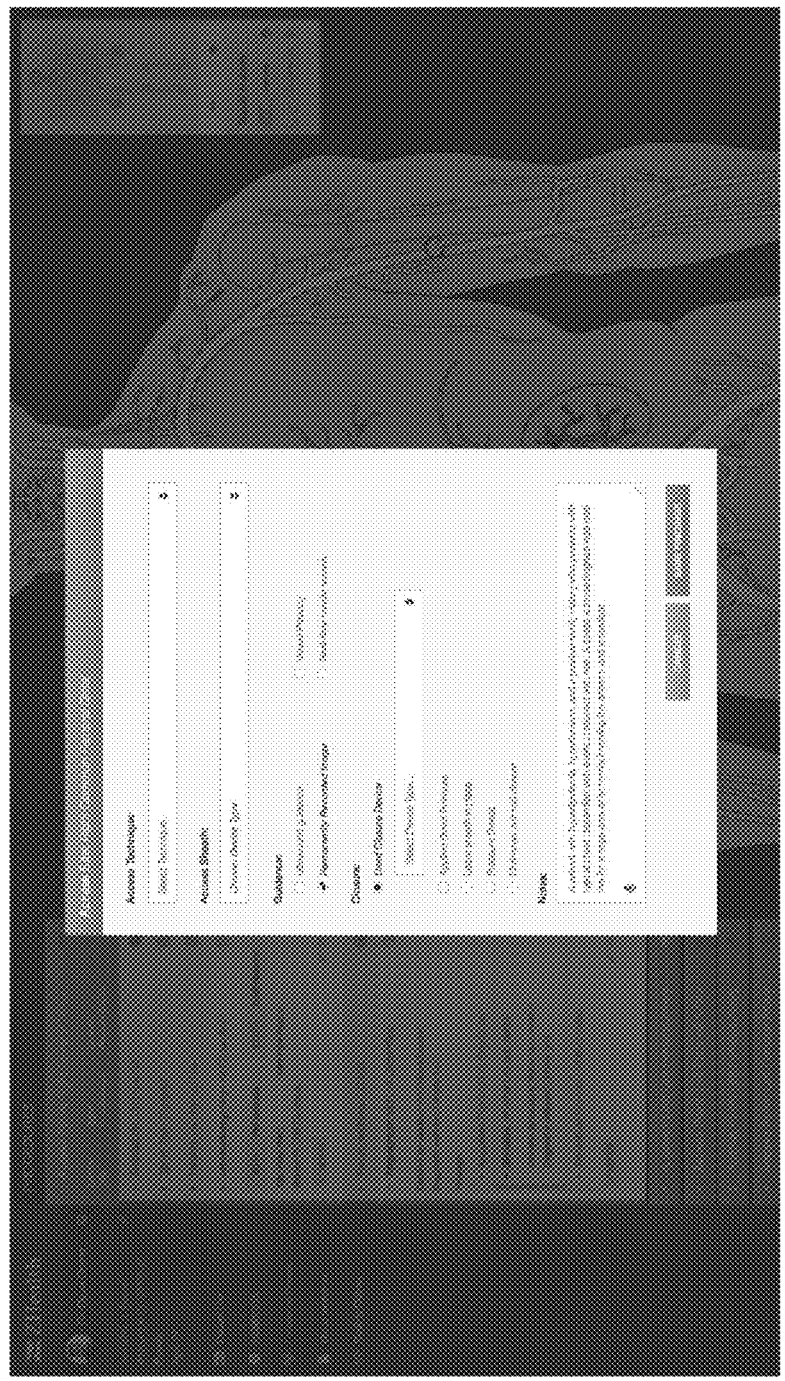
FIG. 25 shows an example of a screen for access site input.
Figure 26:
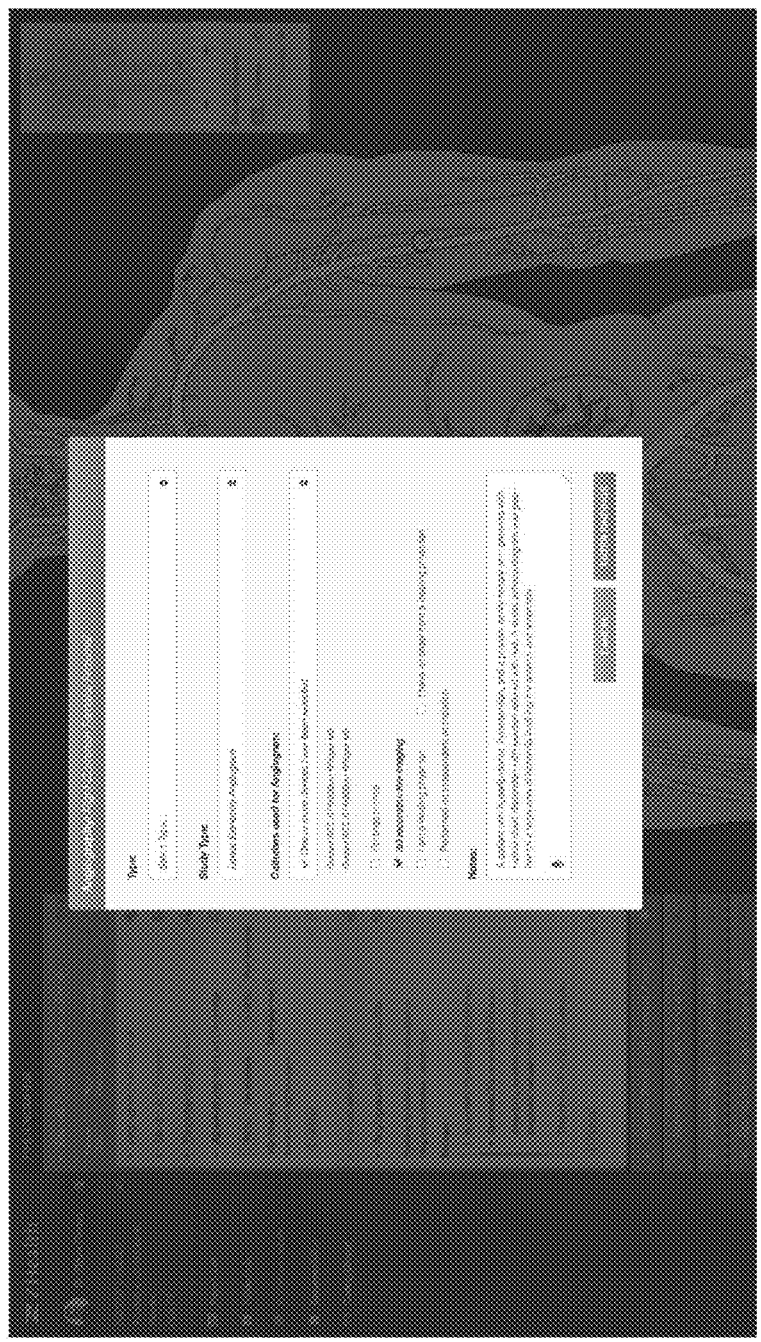
FIG. 26 shows an example of a screen for a procedure input.
Figure 27:
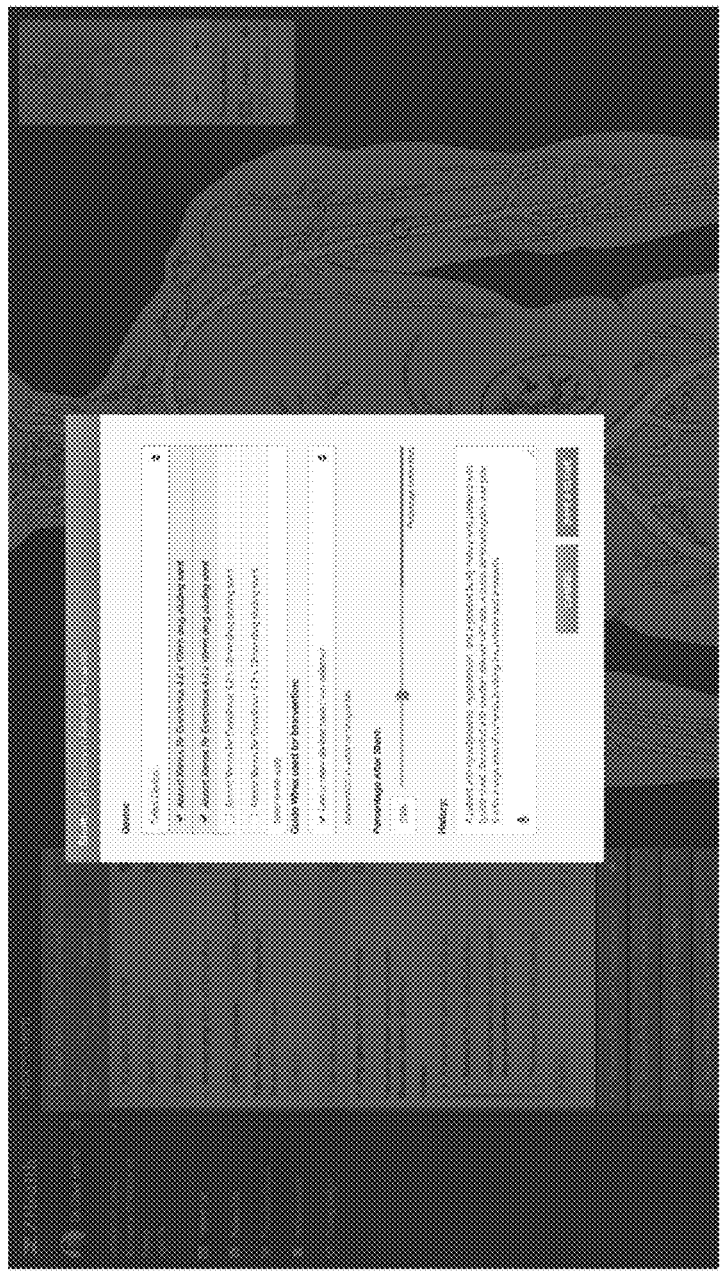
FIG. 27 shows an example of a screen for a device input.
Figure 28:
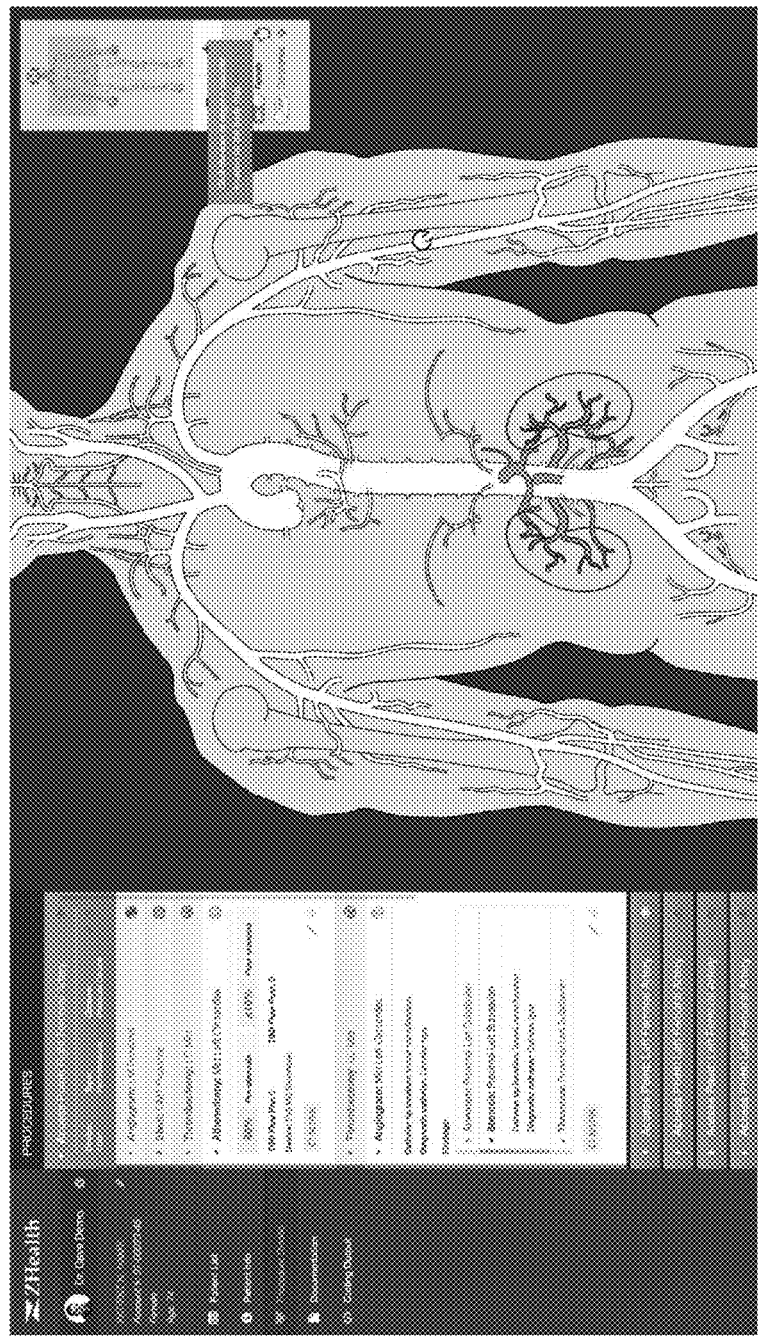
FIG. 28 shows an example of a workspace screen with toggles.
Figure 29:
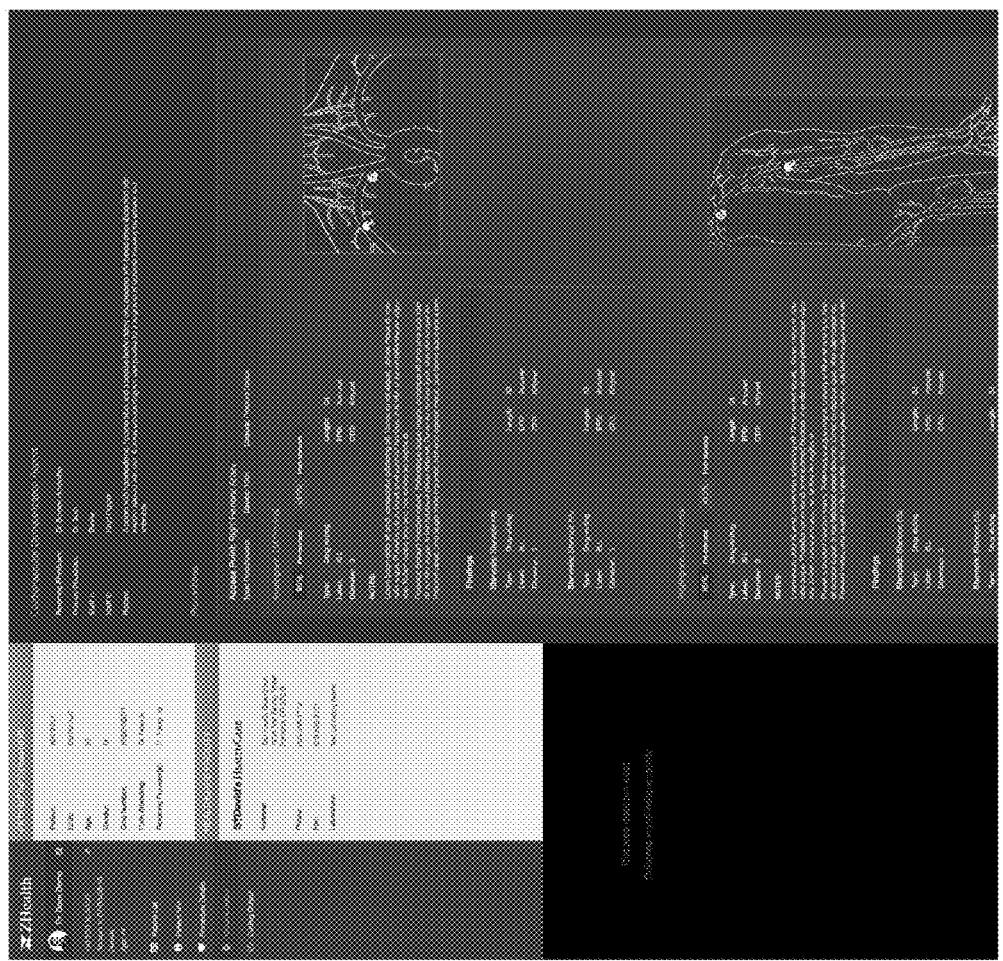
FIG. 29 shows an example of a documentation screen.

10. Perform final bundling (see FIG. 21). Some of the steps performed after the bundling step (such as combining codes or replacing codes) may produce codes that should be bundled. This final bundling step is functionally equivalent to the first bundling step, and allows those later-produced codes to be properly bundled, where appropriate.

In order to provide a context for the various aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), network PCs, minicomputers, mainframe computers, embedded systems, distributed computing environments, and the like.

Embodiments of the invention may be implemented in the form of computer-executable instructions, such as program code or program modules, being executed by a computer or computing device. Program code or modules may include programs, objections, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices.

In one embodiment, a computer system comprises multiple client devices in communication with at least one server device through or over a network. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C#, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A machine for documenting a medical procedure and generating corresponding Current Procedural Terminology (CPT) codes, comprising:
a microprocessor coupled to a memory, wherein the microprocessor is programmed to document a medical procedure and generate CPT codes by:
displaying a graphical nodal map with interactive anatomical charts of a patient, wherein the graphical nodal map is an accurate map customized case to case for the particular patient;
prompting a user to indicate properties about one or more procedures with multiple steps in a case related to said patient using the graphical nodal map as an input interface, wherein said properties includes location information, medical necessity information, and device information for each of said multiple steps;
creating one or more custom transient regions of the graphical nodal map in memory, where medical procedures inside one custom transient region must be different than medical procedures outside the custom transient region;
providing active, context-based guidance to the user as to the entry of medical necessity information so that each step of the procedure is directly documented, and requiring entry of such information in required detail sufficient to support the generated CPT code or codes;
obtaining a first set of rules for determining medical coding based on patient anatomy, procedures performed, and medical necessity of said performed procedures;
obtaining said patient procedure data;
automatically generating, using an atomic code map, one or more atomic codes for each of said procedures in the case, wherein each said atomic code is based on what was done in the procedure and where it was done, and atomic codes retain the properties of the procedures that produced them;
automatically bundling atomic codes where a single code applies to multiple procedures performed in a certain area of the body;
automatically combining multiple atomic codes into a single new atomic code, wherein the new atomic code includes procedure properties that were identical in the multiple atomic codes being combined;
optionally changing of an atomic code to a different atomic code without affecting any other atomic codes generated for the case;
determining one or more anatomic modifiers based on the physical location of one or more particular atomic codes on the patient nodal map;
automatically adding said one or more anatomic modifiers to said one or more particular atomic codes; and
associating said one or more generated atomic codes with the corresponding one or more procedures in a database in electronic communication with said microprocessor.

2. The machine of claim 1, wherein the microprocessor is programmed to generate one or more CPT codes by:
obtaining a second set of rules for Medicare code conformity; and
automatically removing any generated atomic codes that unbillable in combination with each other as determined by application of the second set of rules; and
automatically modifying or adjusting one or more atomic codes by applying said second set of rules to the one or more atomic codes.

3. The machine of claim 2, wherein the microprocessor is programmed to generate one or more CPT codes by:
removing one or more atomic codes that exceed a predetermined maximum number of codes, wherein the maximum number of codes is determined based on code location or the number of a particular code; and
repeating the bundling of atomic codes.

4. The machine of claim 1, further comprising the step of changing an atomic code to a different atomic code without affecting any other atomic codes generated for the case.

5. A method for documenting a medical procedure and generating corresponding Current Procedural Terminology (CPT) codes, comprising:
displaying, using a microprocessor coupled to a memory, a graphical nodal map with interactive anatomical charts of a patient, wherein the graphical nodal map is an accurate map customized case to case for the particular patient;

prompting, using said microprocessor, a user to indicate properties about one or more procedures with multiple steps in a case related to said patient using the graphical nodal map as an input interface, wherein said properties includes location information, medical necessity information, and device information for each of said multiple steps;

creating one or more custom transient regions of the graphical nodal map in memory, where medical procedures inside one custom transient region must be different than medical procedures outside the custom transient region;

providing active, context-based guidance to the user as to the entry of medical necessity information so that each step of the procedure is directly documented, and requiring entry of such information in required detail sufficient to support the generated CPT code or codes;

obtaining a first set of rules for determining medical coding based on patient anatomy, procedures performed, and medical necessity of said performed procedures;

obtaining said patient procedure data in electronic form;

automatically generating, using an atomic code map, one or more atomic codes for each of said procedures in the case, wherein each said atomic code is based on what was done in the procedure and where it was done, and atomic codes retain the properties of the procedures that produced them;

automatically bundling atomic codes where a single code applies to multiple procedures performed in a certain area of the body;

automatically combining multiple atomic codes into a single new atomic code, wherein the new atomic code includes procedure properties that were identical in the multiple atomic codes being combined;

determining one or more anatomic modifiers based on the physical location of one or more particular atomic codes on the patient nodal map;

automatically adding said one or more anatomic modifiers to said one or more particular atomic codes; and associating said one or more generated atomic codes with the corresponding one or more procedures in a database in electronic communication with said microprocessor.

6. The method of claim 5, further comprising the steps of:
obtaining a second set of rules for Medicare code conformity; and
automatically removing or modifying one or more atomic codes by applying said second set of rules to the one or more atomic codes.

7. The method of claim 6, further comprising the steps of:
removing one or more atomic codes that exceed a predetermined maximum number of codes, wherein the maximum number of codes is determined based on code location or the number of a particular code; and
repeating the bundling of atomic codes.

8. The method of claim 5, further comprising the step of changing an atomic code to a different atomic code without affecting any other atomic codes generated for the case.

* * * * *